United States Patent
Marx

[11] Patent Number: 6,059,749
[45] Date of Patent: *May 9, 2000

[54] FIBRIN SEALANT GLUE-GUN WITH INSERTABLE COMPRESSED GAS CARTRIDGE AND LUER-TYPE RESERVOIR CONNECTORS

[75] Inventor: Gerard Marx, New York, N.Y.

[73] Assignee: New York Blood Center, New York, N.Y.

[*] Notice: This patent is subject to a terminal disclaimer.

[21] Appl. No.: 08/816,984

[22] Filed: Mar. 13, 1997

Related U.S. Application Data

[63] Continuation-in-part of application No. 08/615,651, Mar. 13, 1996.

[51] Int. Cl.⁷ .......................... A61M 37/00; A61M 5/00; A61M 11/00; A61B 17/08
[52] U.S. Cl. .......................... 604/82; 604/191; 606/213; 128/200.21
[58] Field of Search ................. 604/82, 191, 11, 604/310; 606/213, 214; 128/200.14, 200.21; 222/478, 129, 136, 482, 485, 491

[56] References Cited

U.S. PATENT DOCUMENTS

| | | | |
|---|---|---|---|
| 4,359,049 | 11/1982 | Redl et al. | 604/82 |
| 4,874,368 | 10/1989 | Miller et al. | 604/82 |
| 4,902,281 | 2/1990 | Avoy | 604/191 |
| 4,978,336 | 12/1990 | Capozzi et al. | 604/82 |
| 4,979,942 | 12/1990 | Wolf et al. | 604/83 |
| 5,582,596 | 12/1996 | Fukunaga et al. | 604/191 |
| 5,665,067 | 9/1997 | Linder et al. | 604/82 |
| 5,814,022 | 9/1998 | Antenavich et al. | 604/191 |

*Primary Examiner*—Ronald Stright
*Assistant Examiner*—Michael J. Hayes
*Attorney, Agent, or Firm*—Amster, Rothstein & Ebenstein

[57] ABSTRACT

An applicator for dispensing a substance comprising first and a second components of any mixture of fluids for either medical or other applications, in an exemplary application, a biological adhesive, such as a fibrin sealant, wherein the applicator comprises a housing having a first dispensing conduit for dispensing the first component and a second dispensing conduit for dispensing the second component. A pressure supply conduit is in communication with the dispensing conduits and both a first reservoir containing the first component, and a second reservoir containing the second component. A cartridge containing a biologically compatible compressed gas may be attached to the pressure supply conduit. The first and second reservoirs may each be provided with a luer fitting to facilitate attachment to a supply of the first component and the second component, respectively. A first pressure regulator, also in communication with the first reservoir, controls the pressure supplied through the pressure supply conduit to the first reservoir and a second pressure regulator, also in communication with the second reservoir, controls the pressure supplied through the pressure supply conduit to the second reservoir. The pressure regulators may be pressure regulating screws or valves, or they may comprise dispensing conduits having various cross sectional areas or reservoir conduits having various cross sectional areas. The applicator dispenses the first and second components, typically a thrombin solution and a fibrinogen solution, in controlled proportions by adjustment of the pressure regulators.

13 Claims, 19 Drawing Sheets

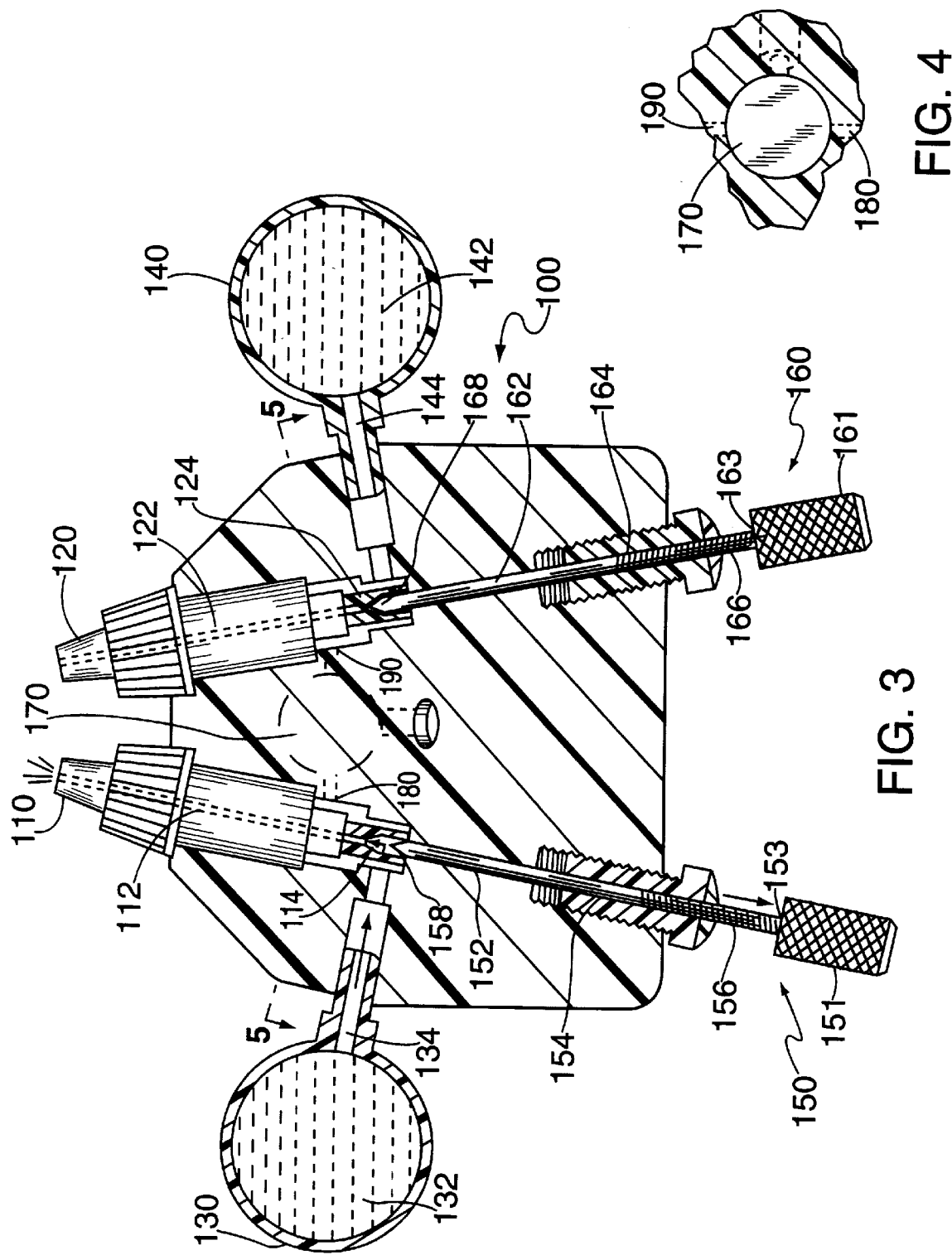

6,059,749

FIBRIN SEALANT GLUE-GUN WITH INSERTABLE COMPRESSED GAS CARTRIDGE AND LUER-TYPE RESERVOIR CONNECTORS

This Application is a Continuation-In-Part of U.S. application Ser. No. 08/615,651, filed Mar. 13, 1996.

BACKGROUND OF THE INVENTION

1. Field of the Invention

This invention relates generally to an applicator for dispensing a mixture of first and second component fluids for medical and other applications, and more particularly, to an apparatus and method for applying a biological adhesive to tissues or organs for sealing wounds and stopping bleeding or to coat prosthetic devices, the apparatus adapted for use with rechargeable or disposable cartridges containing a biologically compatible compressed gas, and further having reservoirs for the first and second components with luer connectors to facilitate attachment to a supply of the first and second components.

2. Description of Related Art

Biological adhesives, such as fibrin sealants, are used to seal wounds and stop bleeding. The components of fibrin sealants include a solution containing thrombin and a solution containing fibrinogen. The solution containing thrombin generally has a relative viscosity of approximately 1.0. The solution containing fibrinogen, on the other hand, can have various relative viscosities depending upon the concentration of fibrinogen. Along those lines, U.S. Pat. No. 2,533,004 to Ferry is directed to various fibrin sealants using different concentrations of fibrinogen and thrombin solutions. Accordingly, an applicator must effectively dispense components having various viscosities. Furthermore, due to the varying viscosities of the solutions, as well as the need for varying adhesive properties, the proportion of the thrombin solution dispensed in relation to the dispensed fibrinogen solution must be controllable.

Although various types of applicators for fibrin sealant have previously been used, such prior applicators have failed to incorporate any structure and method for varying the dispensed proportions of the thrombin solution relative to the fibrinogen solution. U.S. Pat. No. 4,735,616 to Eibl et al. is directed to an arrangement for applying a biological adhesive. The Eibl arrangement includes syringe bodies having equal effective strokes yet different cross-sectional areas. Due to the difference in cross-sectional areas of the two syringes, the ratio of fluid in one syringe that is dispensed relative to the amount of fluid in the second syringe that is dispensed does not equal 1. The device does not allow varying proportions of the fluid to be dispensed. In order for different proportions of the fluids to be dispensed, the syringe must be replaced with another syringe having a different cross-sectional area. As such, these earlier devices prove to be quite cumbersome in use.

Furthermore, previous applicators for dispensing a biological adhesive require the manual exertion of a force on the components so that they may be expelled from the applicator. Typically, a manual force is exerted on the components by means of a standard one-way syringe. This type of arrangement is shown in U.S. Pat. Nos. 4,359,049 and 4,631,055 to Redl et al. Although the embodiments of Redl et al. utilize a pressurized gas, the devices disclosed therein require a manual force to expel the adhesive as the gas is used to merely atomize the adhesive. See U.S. Pat. No. 4,631,055 Col. 3, lines 41–48; U.S. Pat. No. 4,359,049 Col 3, lines 54–57. Manually exerting a force on the components can make application of the adhesive awkward, imprecise, and wasteful.

Similarly, although a syringe-type arrangement is avoided in U.S. Pat. No. 4,902,281 to Avoy, that patent requires a manually exerted force to be applied to the adhesive components. The Avoy patent is directed to the use of a pumping mechanism to expel the adhesive components from the applicator. In order to achieve the desired spray pattern, an abrupt depression of the pumping mechanism must be applied. Like the syringe arrangements, such an applicator is awkward, imprecise, and results in wasted adhesive.

Known devices for applying biological adhesives also have the disadvantage of being difficult to reuse. Once the various components that comprise the adhesive are used up, the supplies must be replenished. In an applicator using a syringe-type arrangement, such as disclosed in the U.S. Patents to Redl et al. discussed above, and in U.S. Pat. No. 4,979,942 to Wolf et al., replenishing the supply of components includes removing a clip which couples the two syringe plungers, detaching the syringes from a form of "Y" connector, removing the syringes from the holder, inserting new syringes, affixing the syringes to the "Y" connector, and replacing the plunger clip. In an application where time is of the essence, such a lengthy replenishing process is impractical and cumbersome.

The reloading procedure in U.S. Pat. No. 4,902,201 to Avoy is similarly inefficient and cumbersome. Replenishing the component solutions involves unlatching the door, opening the housing, removing the spent containers, replacing the containers and closing the housing. Like the replenishing procedure of the syringe-based applicators, this, too, is an involved, time consuming process.

Users of the known applicators encounter an additional difficulty when replenishing the supply of solutions. If a different combination of components is to be used in the applicator, the applications must be cleaned or, in a syringe-type arrangement, the "Y" connector must be replaced. Cleaning the applicator can be time consuming and replacing parts of the applicator is wasteful and non-economical.

OBJECTS OF THE INVENTION

Thus, it is a primary objective of the present invention to provide a fibrin sealant applicator which can vary the dispensed ratio of thrombin solution to fibrinogen solution without requiring replacement of mechanical elements.

It is another object of the present invention to provide a fibrin sealant applicator wherein a pressurized gas is employed to expel the adhesive components.

It is another object of the invention to provide a fibrin sealant applicator for use with a disposable or rechargeable cartridge of a biologically compatible compressed gas to expel the adhesive components.

It is yet another object of the present invention to provide a fibrin sealant applicator which is precise and avoids wasting adhesive solutions.

It is still another object of the present invention to provide a fibrin sealant applicator wherein the component solutions are easily replenished without waste.

It is another object of the present invention to provide the component solutions in removable reservoirs to facilitate ease of replenishing the component solutions.

It is another object of the present invention to provide a fibrin sealant applicator which is reusable with different component solutions.

It is yet another object of the present invention to provide a fibrin sealant applicator which is self-cleaning.

It is yet another object of the present invention to provide a fibrin sealant applicator which dispenses a homogeneous mixture of components.

It is still another object of the present invention to provide a fibrin sealant applicator adapted for easily connecting a supply of the component solutions.

SUMMARY OF THE INVENTION

In accordance with the aforementioned objects, the present invention provides an applicator for dispensing a first component and a second component of a biological adhesive. The biological adhesive may be, but is not limited to, a fibrin sealant. The applicator comprises a housing having a first dispensing conduit for dispensing the first component and a second dispensing conduit for dispensing the second component. A pressure supply conduit is in communication with the dispensing conduits and both a first reservoir containing the first component, and a second reservoir containing the second component. The pressure supply conduit communicates with an external source of air, or a detachable cartridge of a biologically compatible compressed gas. The first and second reservoirs may include luer connectors to facilitate attachment to a supply of the first component and the second component, respectively. A first pressure regulator, also in communication with the first reservoir, controls the pressure supplied through the pressure supply conduit to the first reservoir and a second pressure regulator, also in communication with the second reservoir, controls the pressure supplied through the pressure supply conduit to said second reservoir. In alternate embodiments, the pressure regulators are pressure regulating screws, valves, dispensing conduits having various cross sectional areas, and reservoir conduits having various cross sectional areas. The first and second components, typically a thrombin solution and a fibrinogen solution, are dispensed in controlled proportions by adjusting the pressure regulators or by choosing an appropriate controlling bore size for the flow of liquids.

BRIEF DESCRIPTION OF THE DRAWINGS

FIG. 3 is an elevated sectional view of the sprayer head in FIG. 2 along line 3—3;

FIG. 4 is a partial sectional view of the sprayer head in FIG. 2 along line 4—4;

DETAILED DESCRIPTION OF THE PREFERRED EMBODIMENTS

Figure 1A:
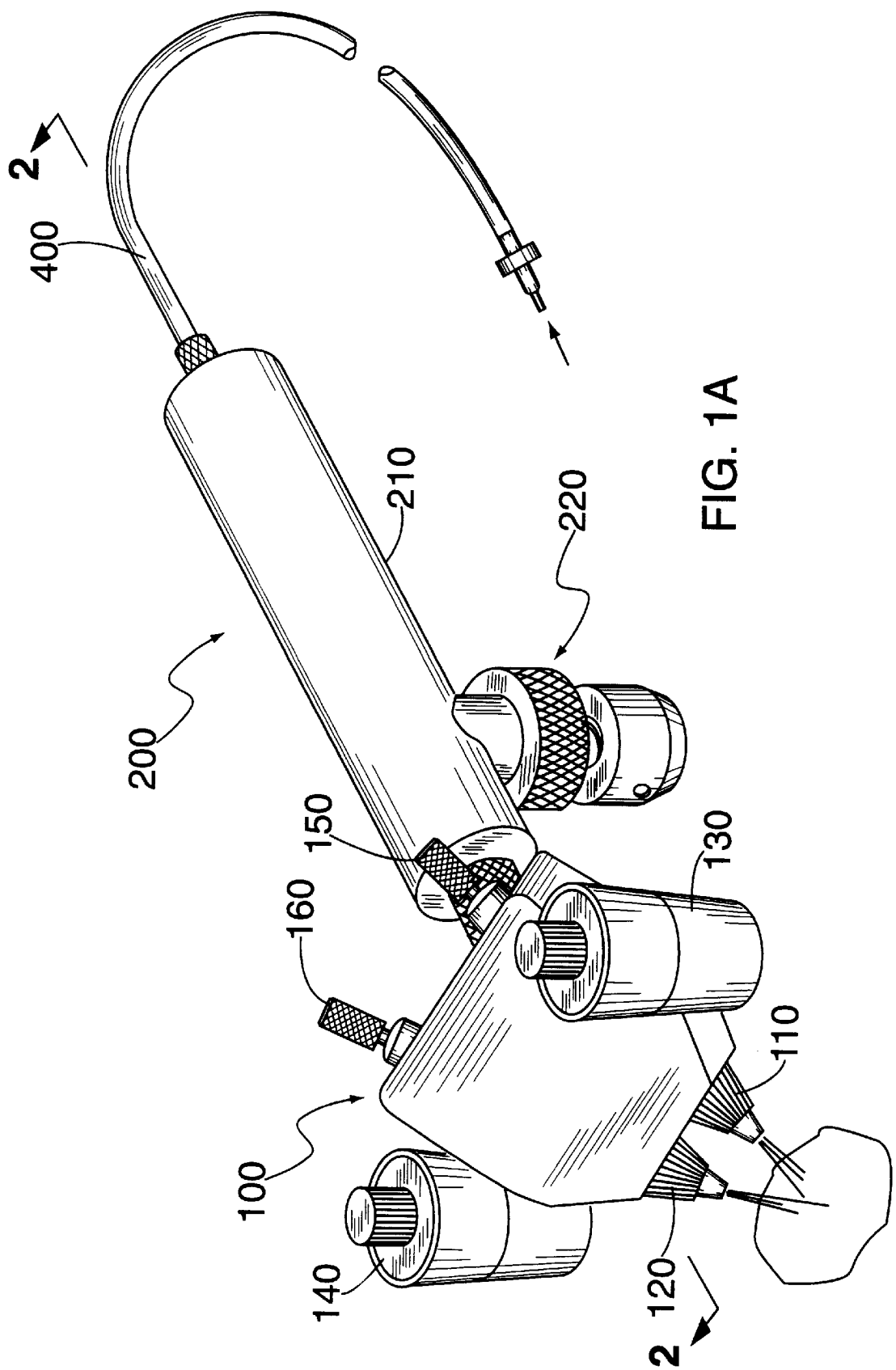
FIG. 1A is a perspective view of a first embodiment of the applicator of the present invention.

Referring to FIG. 1A, an applicator according to one embodiment of the present invention is shown. The applicator consists generally of a spray head 100, a main body 200 and an air supply tube 400, each of these elements being described in greater detail below. The components of the present embodiment are preferably made of medical grade plastics, however it is to be understood that other suitable materials may be used.

The spray head 100 has associated therewith at first reservoir 130 and a second reservoir 140 for containment of biological fluids 132, 142. In the preferred embodiment, the biological fluids 132, 142 are described as a thrombin solution and a fibrinogen solution, which intermix to form a fibrin sealant. It is to be understood, however, that the applicator in accordance with the present invention may be used for an application where two fluids are to be dispensed into a mixture.

The spray head 100 includes a first nozzle 110 and a second nozzle 120 for directing the spray of the fluids contained in the first and second reservoirs 130, 140, respectively. Because the present invention allows for the application of biological fluids having different viscosities, there is associated with the spray head 100 a first pressure regulator 150 and a second pressure regulator 160.

The main body 200 of the applicator consists of a housing 210 and trigger mechanism 220. While the housing 210 in this embodiment is shown as being cylindrical, other shapes and configurations that contribute to the ease of gripping and controlling the applicator may be used. As is described in greater detail below, the trigger mechanism 220 controls the flow of air through the main body 200 into the spray head 100. A flow of air is directed to the main body 200 through the air supply tube 400. Although the present embodiment utilizes the flow of air, it should be noted that other gaseous substances, including those stored in a compressed gas cartridge as described below, or non-reactive liquids may be used.

Figure 2:
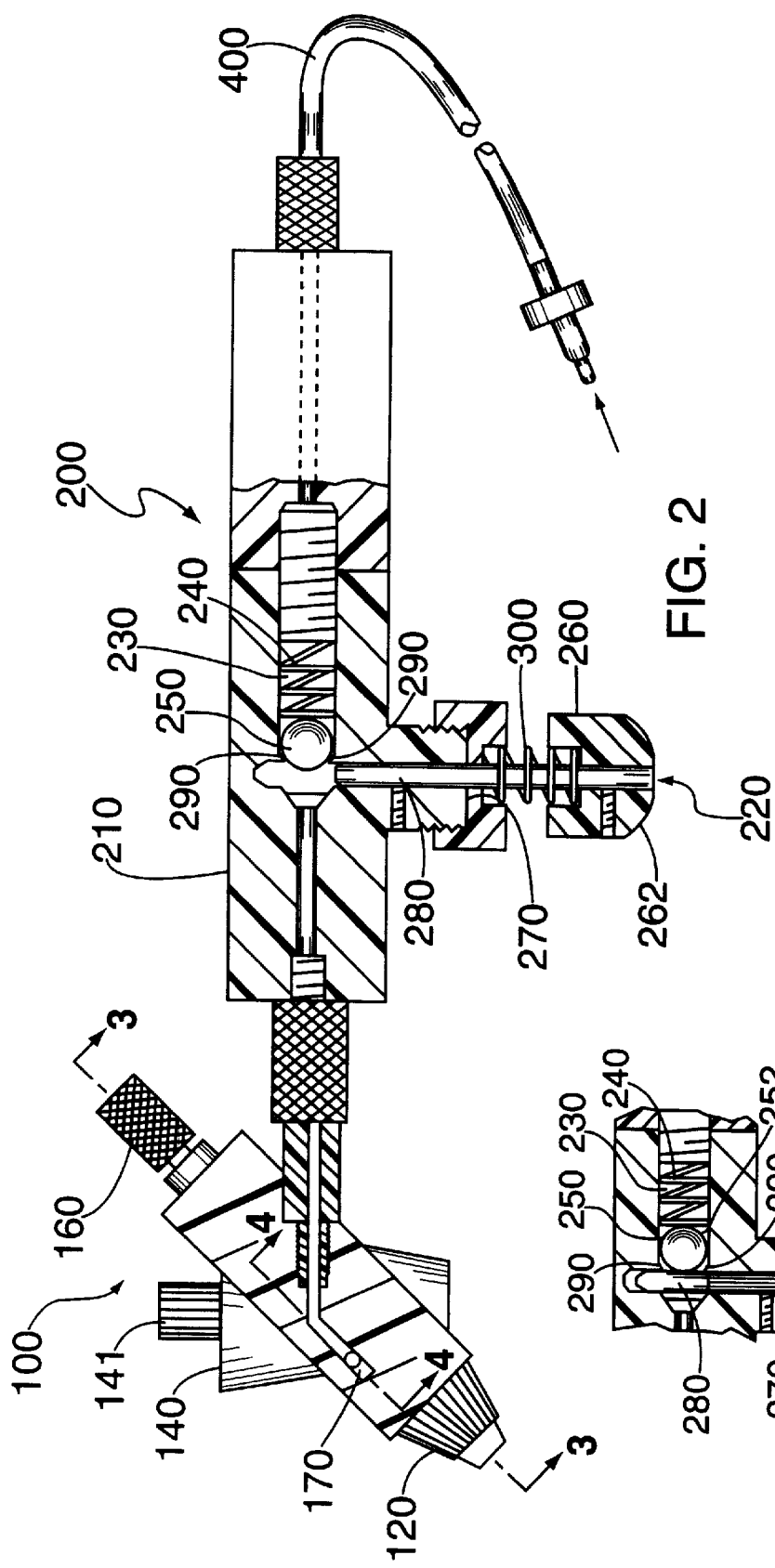
FIG. 2 is a sectional view of the applicator of FIG. 1 along line 2—2.

Referring to FIG. 2, the housing 210 has a bore 230 disposed therethrough. The air supply tube 400 is in communication with the bore 230, thus allowing the flow of air from the air supply tube 400, through the bore 230, and to the spray head 100. The housing 210 has therein a lateral flange 290 extending inward, around the diameter of the bore 230. Spring 240 and bearing 250 are disposed within the bore 230 on the same side of the flange 290 as the air supply tube 400.

FIG. 2 depicts the applicator in an inactivated state with no air flowing therethrough. The trigger mechanism 220 consists of a plunger 260 having a head 262 and a shaft 270. A proximal end 280 of the shaft 270 extends into the body housing 210 and terminates adjacent to the bearing 250. Thus, the proximal end 280 does not interfere with the spring 240 forcing the bearing 250 into contact with the lateral flange 290 of the body housing 210. Because the diameter of the bore 230 at the point of the lateral flange 290 is smaller than the diameter of the bearing 250, a seal is created when the bearing 250 engages the flange 290. Therefore, the flow of air is prevented. The trigger mechanism 220 is maintained in an inactivated state by a spring 300.

Figure 1B:
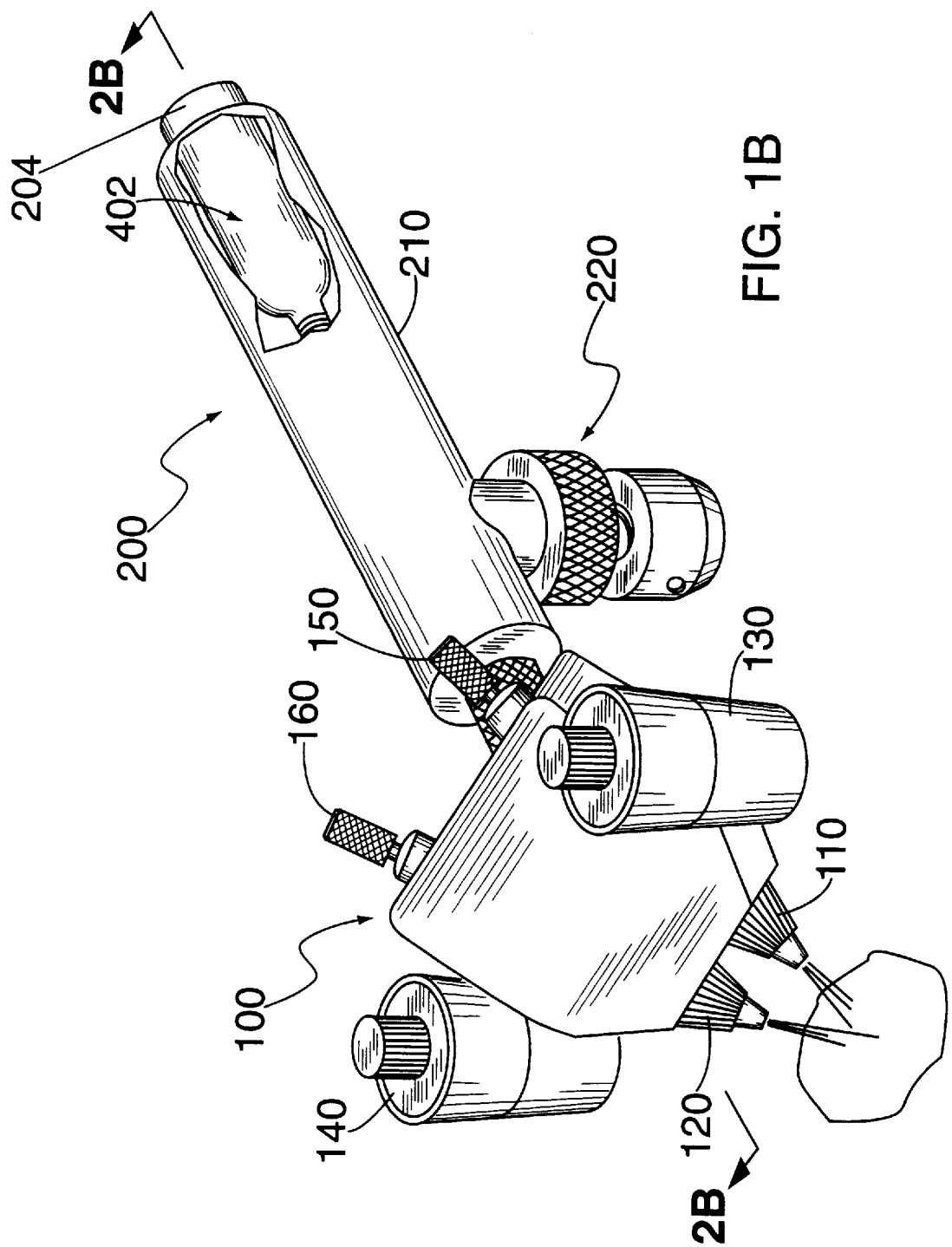
FIG. 1B is an perspective view of an alternative embodiment thereof.
Figure 2A:
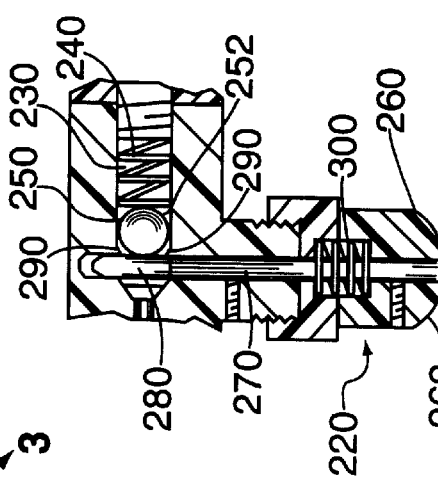
FIG. 2A is a sectional view of the trigger mechanism of the applicator of FIGS. 1A, 1B and 2, showing the trigger mechanism in an activated state.
Figure 2B:
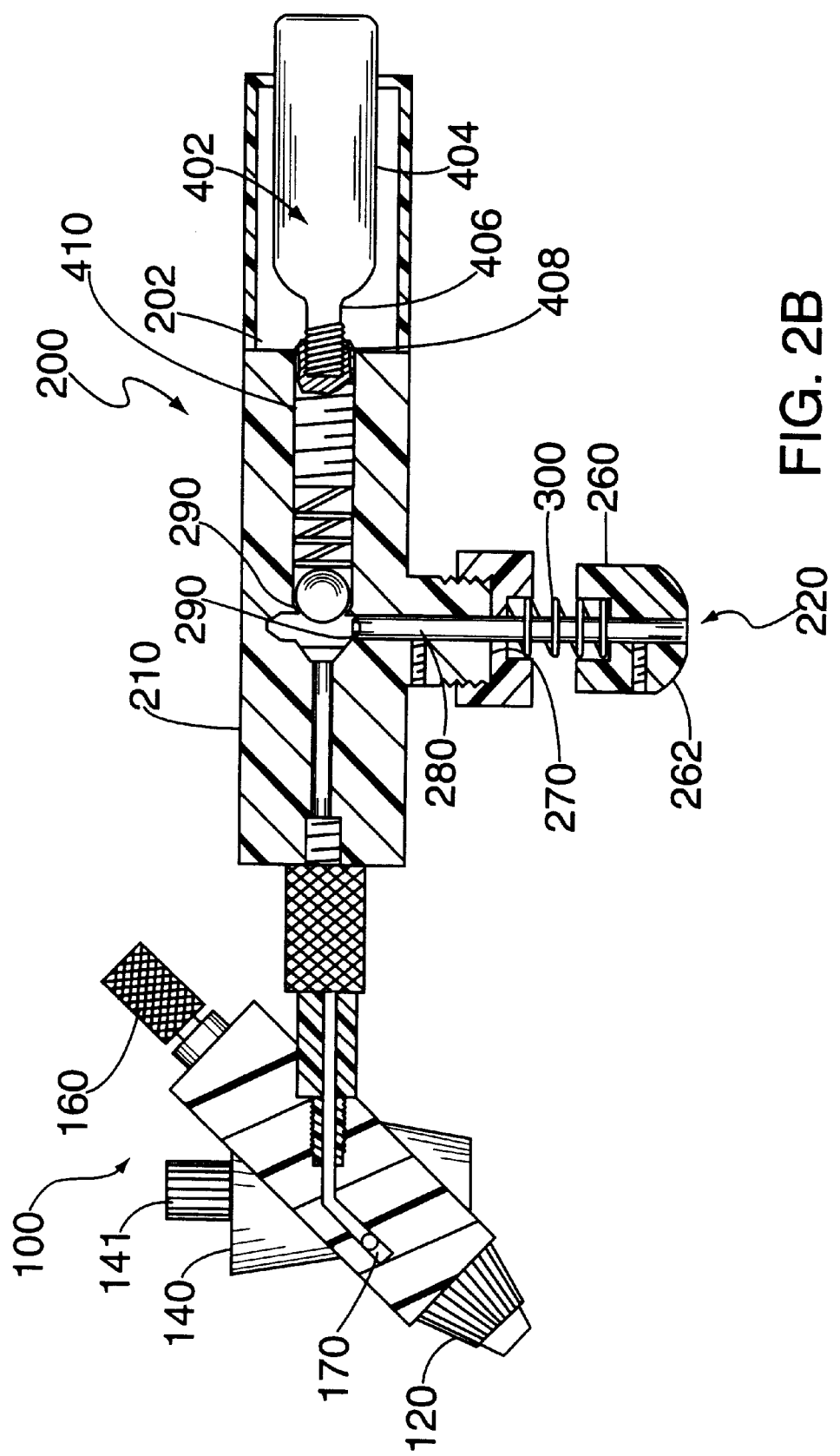
FIG. 2B is a sectional view along line 2B—2B in FIG. 1B.
Figure 5:
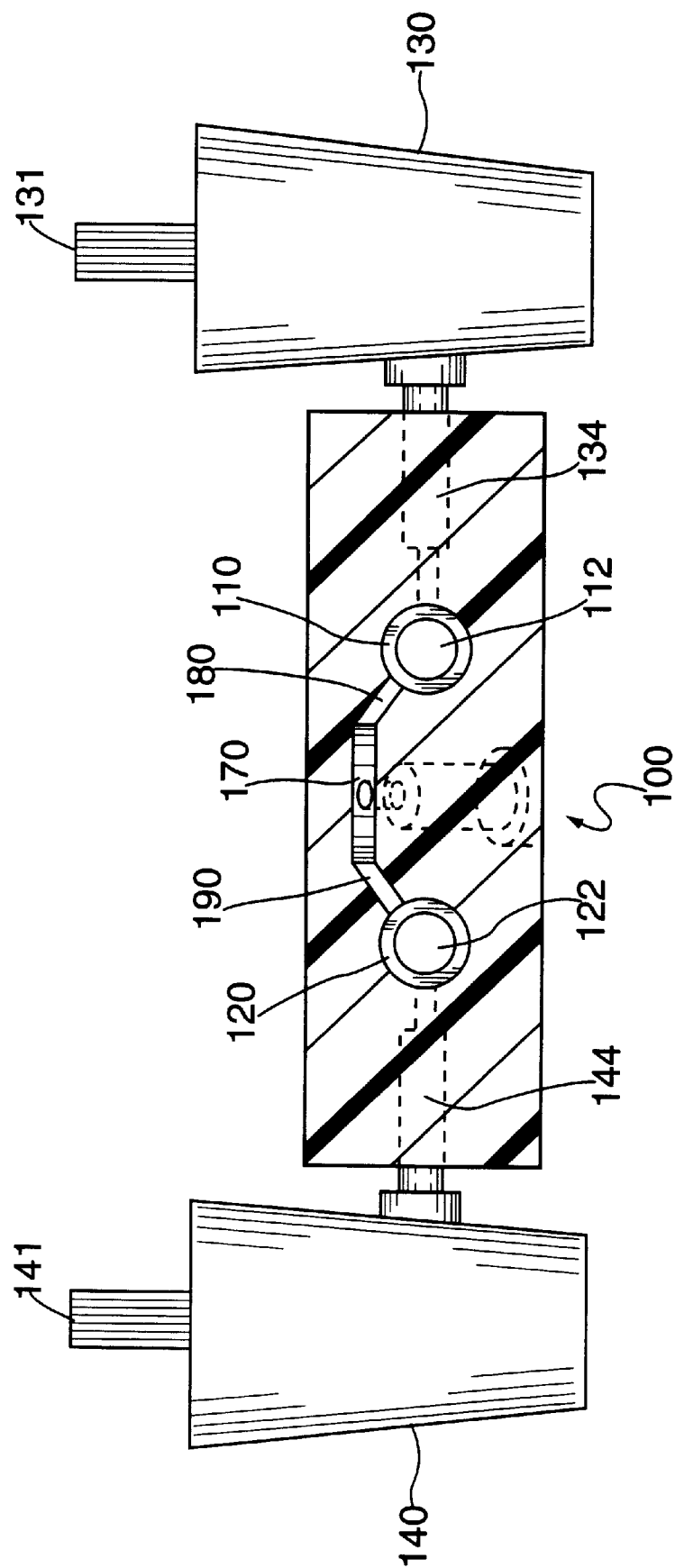
FIG. 5 is a sectional view of the sprayer head in FIG. 3 along line 5—5.

Referring to FIGS. 1B and 2B, there is shown an embodiment wherein the operative pressure medium is supplied from a gas cartridge 402. This obviates the need for any external air supply or pump apparatus. The housing 200 includes a chamber 202 with an access opening 204 at the end thereof to accept the gas cartridge 402. The gas cartridge 402 contains a supply of a biologically compatible compressed gas, e.g., carbon dioxide, helium, or the like, as is well known. The gas cartridge 402 includes a body 404 and a neck 406. The neck 406 may be provided with a retaining flange or external thread 408 as shown. In this connection, the pressure supply bore 230 described above includes a complimentary female thread 410. This enables the treaded neck 406 of the cartridge 402 to be threadably connected to the bore 230. The threaded arrangement is selected so as to provide a sealing effect at the attachment interface in a manner known in the art. Following use of the inventive applicator, where the gas cartridge 402 is depleted, it is simply unthreaded from the bore 230 and discarded or recharged. It is to be understood that the gas cartridge 402 may be attached to the bore 230 using other methods, such as press-fit, snap-fit and the like, the embodiment shown and described being merely exemplary.

Referring now to FIG. 2A, the trigger mechanism 220 in an activated state is illustrated. By applying a force to the plunger head 262 that is parallel to the shaft 270, the spring 300 is compressed, and the shaft 270 is forced further into the housing 210. As the shaft 270 enters the housing 210, the proximal end 280 slidably engages the bearing 250 and forces the bearing 250 away from the flange 290, thereby compressing spring 240. The proximal end 280 of the shaft 270 is preferably conical in shape thereby contributing to the ease with which the bearing 250 is urged away from the flange 290. Because the outside diameter of the bearing 250 and the outside diameter of the end 280 of the shaft 270 are smaller than the diameter of the bore 230, a gap 252 is created. Thus, air flows from the air supply tube 400, into the bore 230, through the gap 252, and into the spray head 100. When the force applied to the plunger 262 is removed, the spring 300 urges the plunger 260 away from the body housing 210, thereby withdrawing the shaft 270 from the bore 230. The spring 240, as well as the pressure of the flowing air, forces the bearing 250 back into engagement with the flange 290, thereby returning the applicator to the inactivated state as depicted in FIG. 2. Although the present invention has been described with a particular trigger mechanism, it is understood that other similar mechanisms may be employed.

Referring to FIG. 3, there is illustrated in greater detail the spray head 100. A first reservoir 130 and a second 140 reservoir for storing a first biological fluid 132 and a second biological fluid 142 are affixed to the spray head 100. The reservoirs 130, 140 are respectively in communication with nozzle bores 112, 122 via conduits 134, 144, respectively. The reservoirs 130, 140 may be permanently affixed to the conduits 134, 144 or, alternatively, the reservoirs 130, 140 may be provided with a luer or other mechanical connection to be made removable to facilitate changing fluids as required. The reservoirs 130, 140 may utilize either a male or female component of a luer mechanism and the conduits 134, 144 are configured with a corresponding structure for engaging therewith.

Although the present embodiment according to the claimed invention depicts a certain form of reservoir, it is to be understood that the applicator can be fitted with any of a number of different reservoirs, including, without limitation, syringes, bags or tubing. Furthermore, although the present embodiment according to the claimed invention has but two reservoirs, it is to be understood that additional reservoirs containing other solutions, such as is disclosed in Applicant's co-pending U.S. patent applications Ser. Nos. 08/465,888, 08/459,345, and 08/460,534, herein incorporated by reference, may be similarly incorporated.

When the trigger mechanism 220 is in an activated state, the air flows from the air supply tube 400, through the housing 210, and into the spray head 100 via a main conduit 170. The air travels from the main conduit 170 through a first conduit 180 and into a first nozzle bore 112 disposed in a first nozzle 110. The air also travels from the main conduit 170 through a second conduit 190 and into a second nozzle bore 122 disposed in the second nozzle 120. The air then exits each of the nozzles 110, 120 to the area of lowest pressure—the external environs. The flow of the air through the first and second conduits 180, 190 and through the first and second bores 112, 122 creates regions of low pressure at each of the proximal ends 114, 124 of the nozzle bores 112, 122, respectively. The nozzles 110, 120 are preferably adjustable so that the angle at which the components of the adhesive are dispensed may be adjustable, thereby allowing the user to adjust the focal point of the component spray.

FIG. 3 also illustrates a first pressure regulator screw 150. The pressure regulator screw 150 is partially disposed within a bore 155 in the spray head 100. The bore 155 and, therefore, the screw 150, are in linear alignment with the first nozzle bore 112. The pressure regulator screw 150 generally comprises a head 151 affixed to the distal end 153 of a shaft 152. The pressure regulator screw shaft 152 has threads 156 for engagement with grooves 154 within the screw bore 155.

Similarly, FIG. 3 also illustrates a second pressure regulator screw 160. This pressure regulator screw 160 is partially disposed within a bore 165 in the spray head 100. The bore 165 and, therefore, the screw 160, are in linear alignment with the second nozzle bore 122. This pressure regulator screw 160, like the screw 150 previously described, generally comprises a head 161 affixed to the distal end 163 of a shaft 162. This pressure regulator screw shaft 162 similarly has threads 166 for engagement with grooves 164 within the screw bore 165.

FIG. 3 illustrates a pressure regulator screw 150 that has had a counterclockwise torque applied thereto. By applying a counterclockwise torque to the head 151 perpendicular to the shaft 152, the screw 150 is disengaged from the nozzle bore 112. The pressure regulator screw 150 is depicted with the proximal end 158 of the shaft disengaged from the proximal end 114 of the nozzle bore 112. The area of low pressure caused by the flow of the gas through bore 112 causes a biological fluid 132 contained in reservoir 130 to be drawn out through the conduit 134 and into the bore 112. The biological fluid 132 is then expelled from the apparatus through the nozzle 110. As shown in this preferred embodiment, the proximal end 158 of the pressure regulator screw 150 is conical in shape so to be engagable with the proximal end 114 of the bore 112, the proximal end 114 being conical in shape.

FIG. 3 also illustrates a pressure regulator screw 160 that has had a clockwise torque applied thereto. By applying a clockwise torque to the head 161 that is perpendicular to the shaft 162, the shaft 162 may be further disposed within the spray head 100 such that the proximal end 168 of the screw 160 engages with and closes off the proximal end 124 of the nozzle bore 122. Like the first pressure regulator screw 150, the proximal end 168 of the second pressure regulator screw 160 is conical in shape so to be engagable with the proximal end 124 of the bore 122, the proximal end 124 being conical in shape.

The second pressure regulator screw 160 is depicted fully disposed within spray head 100 such that the proximal end 168 is fully engaged with the proximal end 124 of the bore 122. Complete engagement of the proximal end 168 of the shaft with the proximal end 124 of the bore prevents the biological fluid 142 contained in the reservoir 140 from flowing through the bore 122.

Although pressure regulator screw 150 is depicted in a fully disengaged state and pressure regulator screw 160 is depicted in a fully engaged state, intermediate positions are possible. By rotating the pressure regulator screws 150, 160, shafts 152, 162 may be selectively positioned within the screw bores 155, 165 such that the proximal end 158, 168 of the shafts are in partial engagement with the proximal ends 114, 124 of the nozzle bores. Such selective positioning of the pressure regulator screws 150, 160 alters the pressure created by the flow of gas through the bores 112, 122 and, consequently, changes the amount of flow of biological fluid 132, 142, from the reservoirs 130, 140, respectively. Because each reservoir 130, 140 has an independent pressure regulator screw 150, 160, associated therewith, the applicator may dispense the first and second biological fluids 132, 142 in different proportions.

In an alternative embodiment, nozzle bores having different diameters may account for components having different viscosities. Increasing the diameter of a nozzle bore creates a greater pressure differential at the bore's proximal end. The greater pressure differential exerts a greater force on the corresponding component, thereby drawing the component out of the reservoir at an increased rate. Conversely, decreasing the diameter of a nozzle bore reduces the force exerted on a component and decreases the rate at which the component is drawn out of the reservoir. Consequently, components with different relative viscosities may be dispensed in different ratios with respect to each other. Thus, the pressure regulator may be defined in terms of the nozzle bore of a specified diameter.

In another alternative embodiment, reservoir conduits having different diameters may allow for the components to be dispensed in different ratios. A larger reservoir conduit allows the component contained therein to flow more freely while a smaller reservoir conduit restricts the flow of such component. Thus, instead of regulating the pressure of the gas, the flow volume of the dispensed biological fluid is controlled at the reservoir. This approach also permits the applicator to dispense different ratios of components having different relative viscosities.

In the present embodiment, the dispensing ratio of the first biological fluid 132 to the second biological fluid 142 ranges generally from 1 to 1 through 1 to 10. Thus, this embodiment is capable of dispensing a first fluid having a relative viscosity of 1.0 and a second fluid having a relative viscosity of 1.0 during a given application and dispensing a first fluid having a relative viscosity of 1.0 and a second fluid having a relative viscosity of 20 during another application.

Regardless of the actual component fluids 132, 142 used, the present embodiment achieves thorough intermixing of the fluids 132, 142 and a homogeneous spray. The applicator delivers a homogeneous spray because a controllable force, other than a manual force, is used to force the fluids 132, 142 from the reservoirs 130, 140 as well as atomize them upon being dispensed. In the external air supply embodiment shown in FIG. 1, air pressure in the range of 25 to 30 pounds per square inch is used. The gas cartridge embodiments or aerosol at a similar pressure may also be used. By controlling the force as described above, the applicator can deliver a slurry or suspension of particles. Furthermore, the present embodiment has the ability achieve such mixtures of particles ranging in size from at least 0.1 to 200 microns. Additionally, these may be regular particles, including, without limitation, spherical proteins or polysaccharidic microbeads or liposomes, or irregular particles, including, without limitation, C18 resin or suspensions of cultured sells such as fibroblasts.

The applicator in accordance with the present embodiment may be reused in an efficient, economical, and sterile manner. By using a first nozzle 110 and a second nozzle 120, intermixing of the component fluids 132, 142 occurs external to the applicator, thereby preventing clogging. Furthermore, by using an external pressure supply to expel the component fluids 132, 142, virtually all of the fluid 132, 142 is drawn out of the reservoirs 130, 140 and forced out of the applicator. If fluid 132, 142 were to remain attached to either the nozzle bores 112, 122 or the conduits 134, 144, valves 131, 141 on the reservoirs 130, 140 could be opened (or in an alternative embodiment, the reservoirs removed) and pressurized air or other gas forced through the applicator. The forced air or gas, with the reservoirs 130, 140 empty, cleans the internal applicator mechanisms thoroughly.

An alternative embodiment of the present invention (not shown) is a modification of the preferred embodiment for use in laproscopic surgery. The modifications to the preferred embodiment include elongating the spray head and reservoirs such that they are tubular and fit within an incision. Alternatively, just the nozzles are elongated so that they are tubular and fit within an incision. The trigger mechanism, as well as the pressure supply, remain outside the patient's body.

Referring now to FIGS. 6–15, several exemplary embodiments of the reservoirs 130, 140 are shown. Since both reservoirs are identical, the following description will refer to reservoir 130 for convenience. Reservoir 130 is generally comprised of a reservoir basin 500 and reservoir insert 502.

Figure 6:
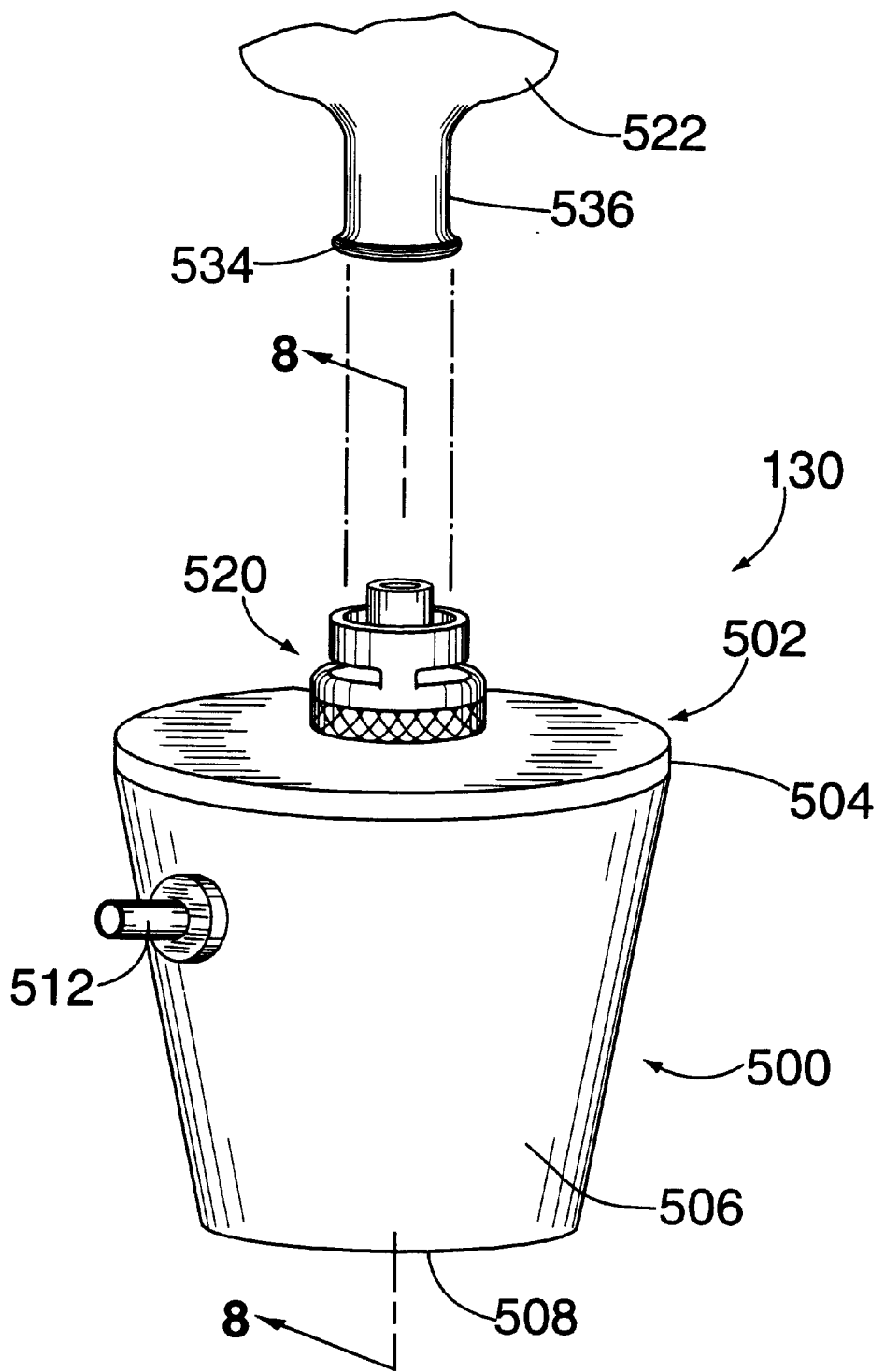
FIG. 6 is a perspective view of a first reservoir embodiment for connecting to a supply of the first or second component.
Figure 7:
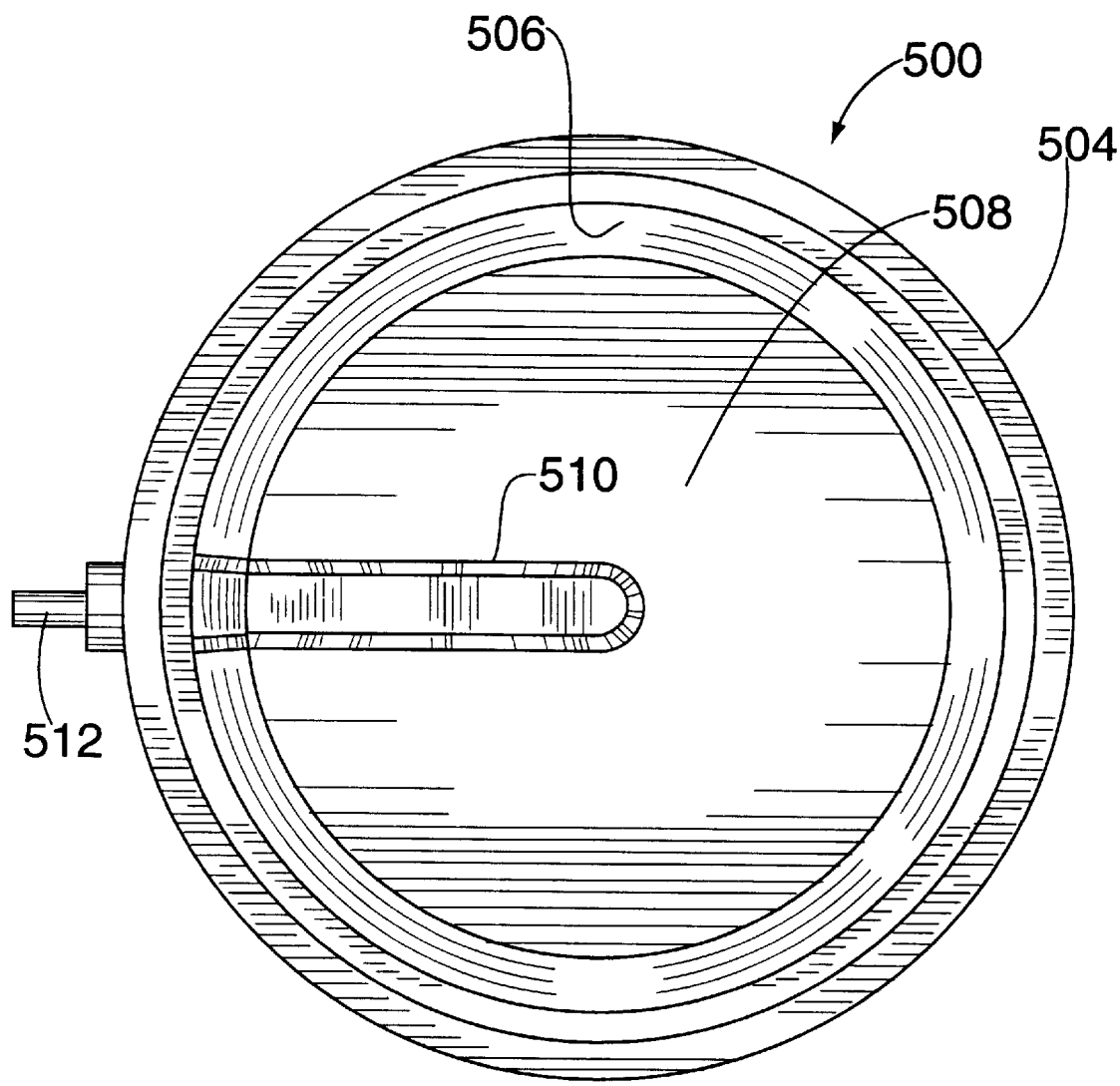
FIG. 7 is a top plan view of a reservoir basin.

As best seen in FIGS. 6 and 7, the reservoir basin 500 includes a top rim 504, sidewall 506 and base 508. A recessed channel 510 extends radially outwards from a central location in the base 508 and up the sidewall 506. An outlet 512 communicates with channel 510, thereby enabling the first component to flow from the first reservoir 130 to the first dispensing conduit 134, and the second component to flow from the second reservoir 140 to the second dispensing conduit 144. The bore size of the outlet 512 may be selected to provide the desired flow rate of each component fluid. By independently selecting the appropriate bore size for the respective fluids 132, 142, the ratio of the components in the mixture may be controlled.

Figure 8:
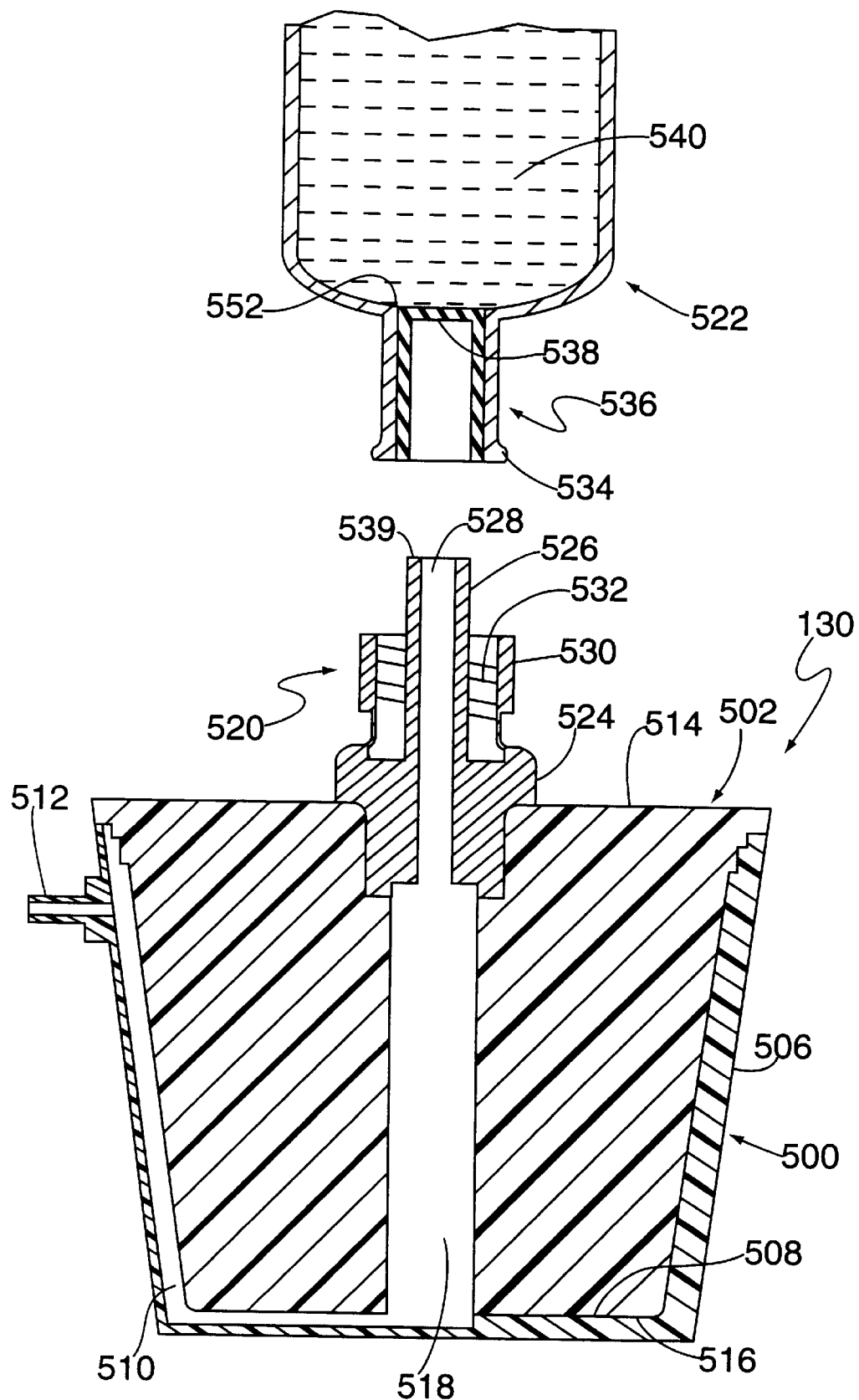
FIG. 8 is an exploded sectional view along line 8—8 in FIG. 7, showing a reservoir prior to attaching a supply of the first or second component.

Referring now to FIGS. 7 and 8, the insert 502 is constructed and arranged to be coaxially disposed and integral with the basin 500. There are several embodiments in connection with this aspect of the invention, so they will be described individually. In the first embodiment, the top end 514 of the insert 502 defines the top end of the reservoir 130, and the bottom end 516 of the insert 502 rests against the base 508 of the basin 500. The insert 502 defines a hollow bore 518 therethrough which provides a passageway to communicate the first component through a luer connector 520 extending from the top end 514 of the insert 502 as shown. The luer connector 520 is of the type well-known in the art, adapted for interfitting engagement with a mating connector 534 associated with a supply of the first component or the second component 522 as described below. The luer connector 520 is attached to the insert 502 by either integrally molding the base area 524 thereof into the insert 502, or by threading the base area 524 into the insert 502 subsequent to molding the insert 502. In the illustrative luer connector 520, an elongated central portion 526 defines a hollow bore 528 therethrough, which communicates with the hollow bore 518 in the insert 502. A concentric portion 530 of luer connector 520 contains a female thread 532 for connecting a mating male connector 534 associated with the neck portion 536 of the supply 522 of the first or second components.

Figure 9:
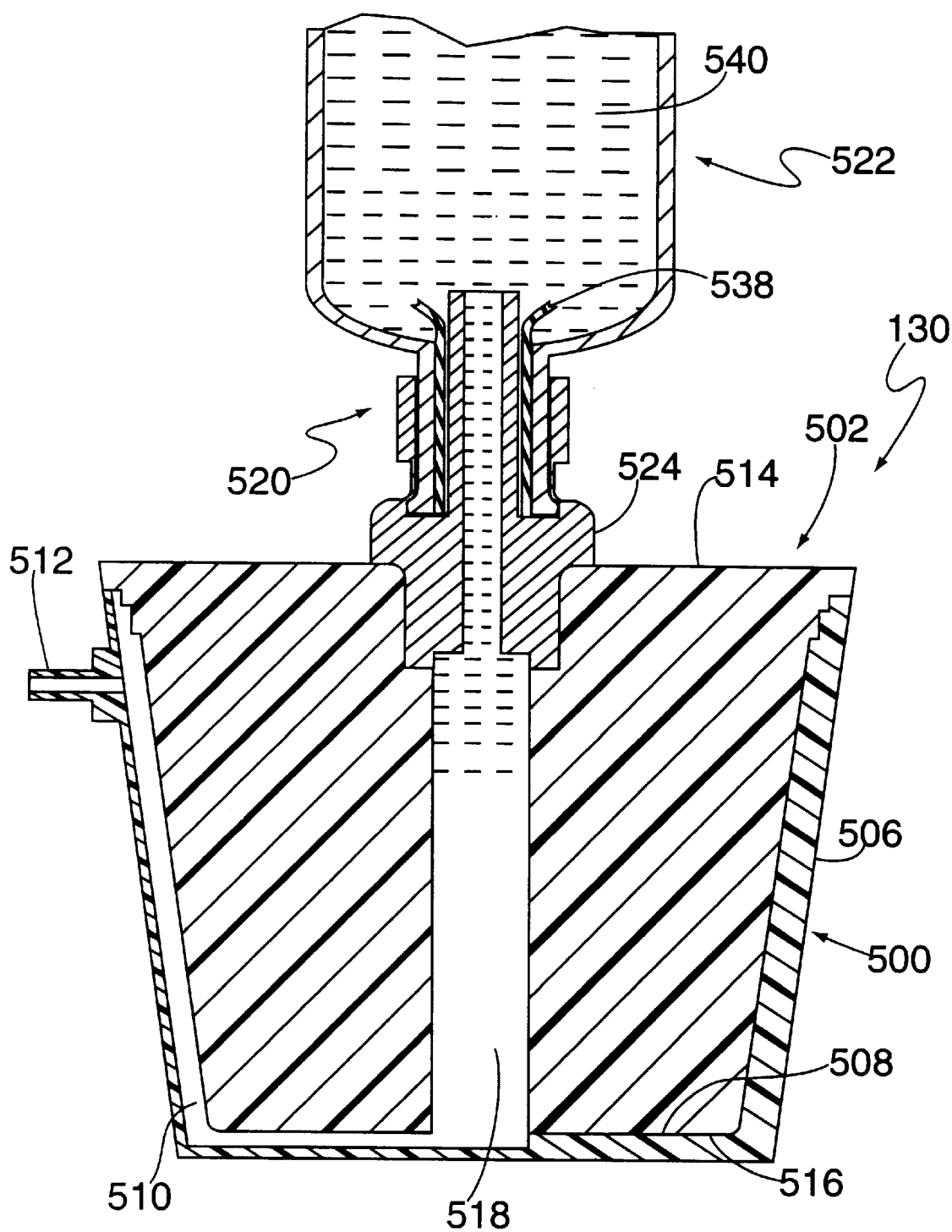
FIG. 9 is a sectional view of the embodiment depicted in FIGS. 6 and 7, showing the supply of the first or second component attached to the reservoir.

In the embodiment shown in FIGS. 8 and 9, the supply 522 includes a cylindrically shaped frangible seal 538 disposed proximal to the internal rim 552 at the opening between the neck portion 536 and the enlarged storage volume generally identified by the reference numeral 540. The seal 538 keeps the liquid components inside the storage volume 540 until it is severed by the top circumferential edge 539 of the elongated central portion 526 of the luer connector 520 when the two components are joined by threading the male connector 534 into the female connector 520 as shown in FIG. 9, thereby allowing the first or second component to flow freely from the internal chamber 541 of the supply 522, through the connection, and into the reservoir 130.

Figure 10:
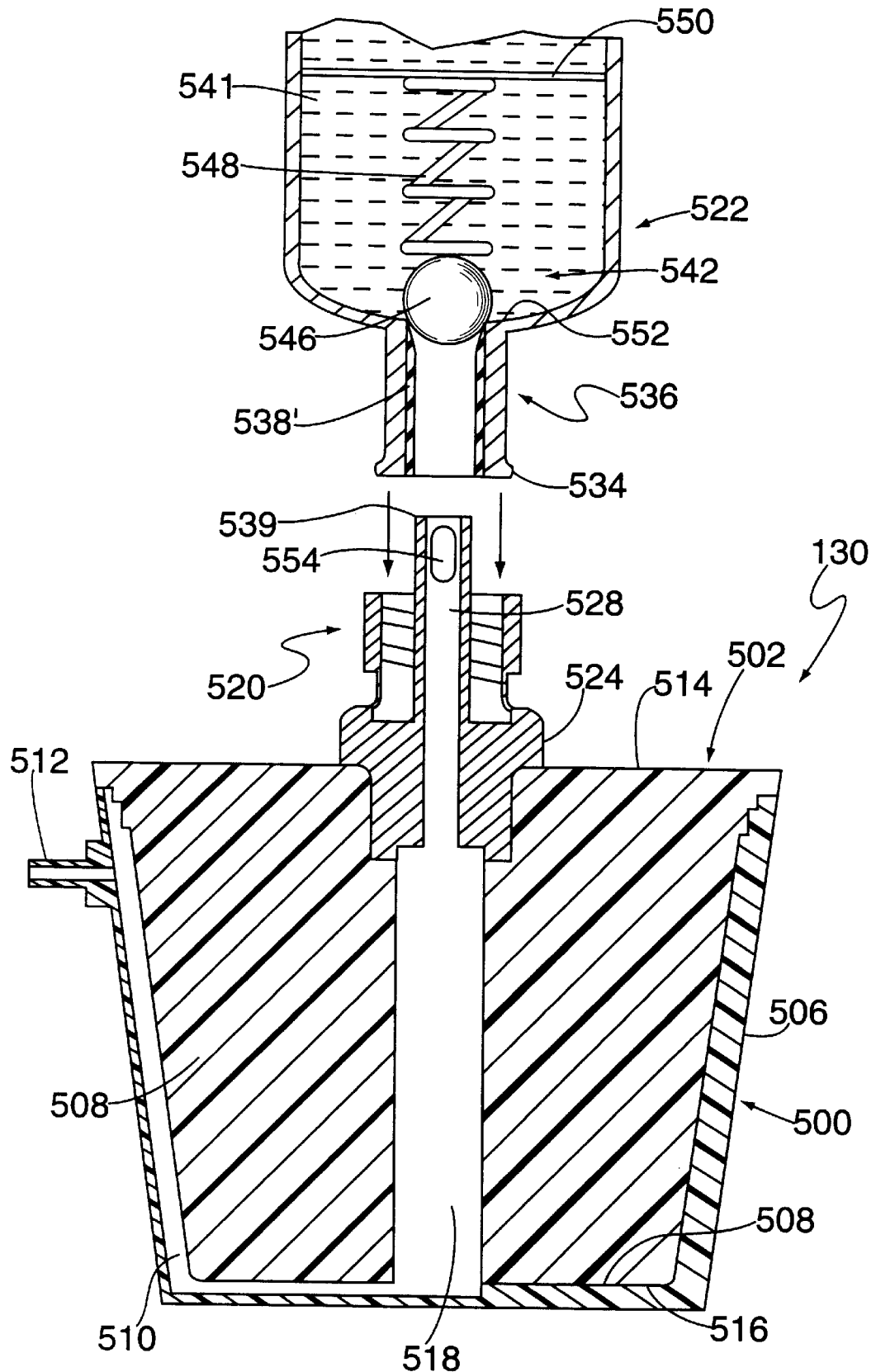
FIG. 10 is an exploded sectional view depicting a modification of the embodiment shown in FIGS. 6–9.
Figure 11:
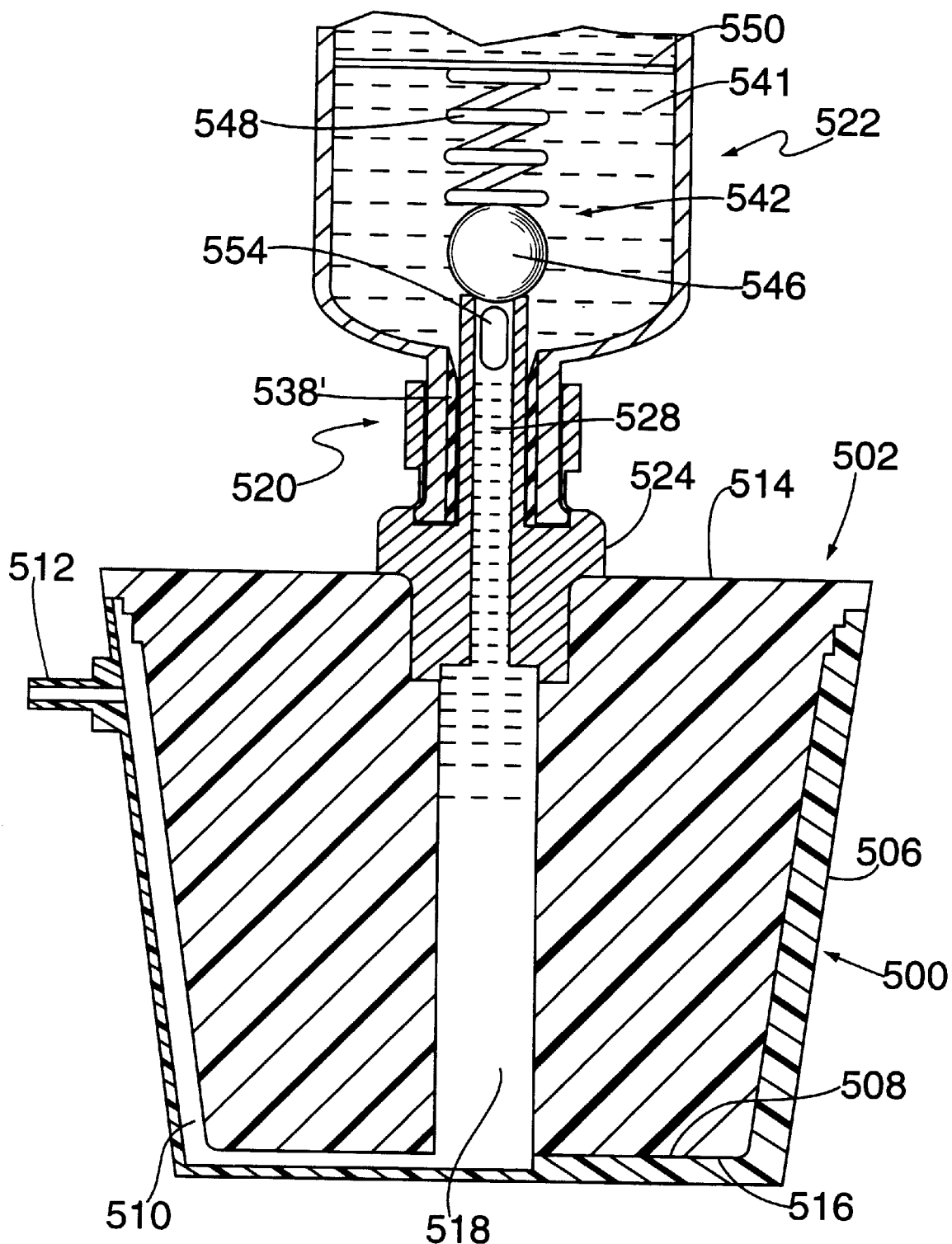
FIG. 11 is a sectional view of the embodiment shown in FIG. 10, depicting the supply of the first or second component attached to the reservoir.

In a second embodiment depicted in FIGS. 10 and 11, the supply 522 is provided with a spring-loaded ball valve 542. The ball valve 542 comprises a ball element 546, and a compression spring 548. The compression spring 548 is attached to the internal structure of the supply 524 by appropriate means, such as the cross-member 550 shown. The ball element 546 is normally biased by the spring 548 such that it seats against the internal rim 552 of the neck portion 536. A cylindrical seal 538' is provided along the inside diameter of the neck portion 536. When the supply 522 is connected to the reservoir 130, the elongated central portion 526 makes contact with and urges the spring-loaded ball element 546 upwardly out of the seated position as shown in FIG. 11. The central portion 526 of the luer connector 520 is provided with at least one slot 554 positioned near the circumferential top edge 539, so as to fluidly communicate the first or second component from the internal chamber 541 of the supply 522 to the hollow bore 528 and into the reservoir 130.

Figure 12:
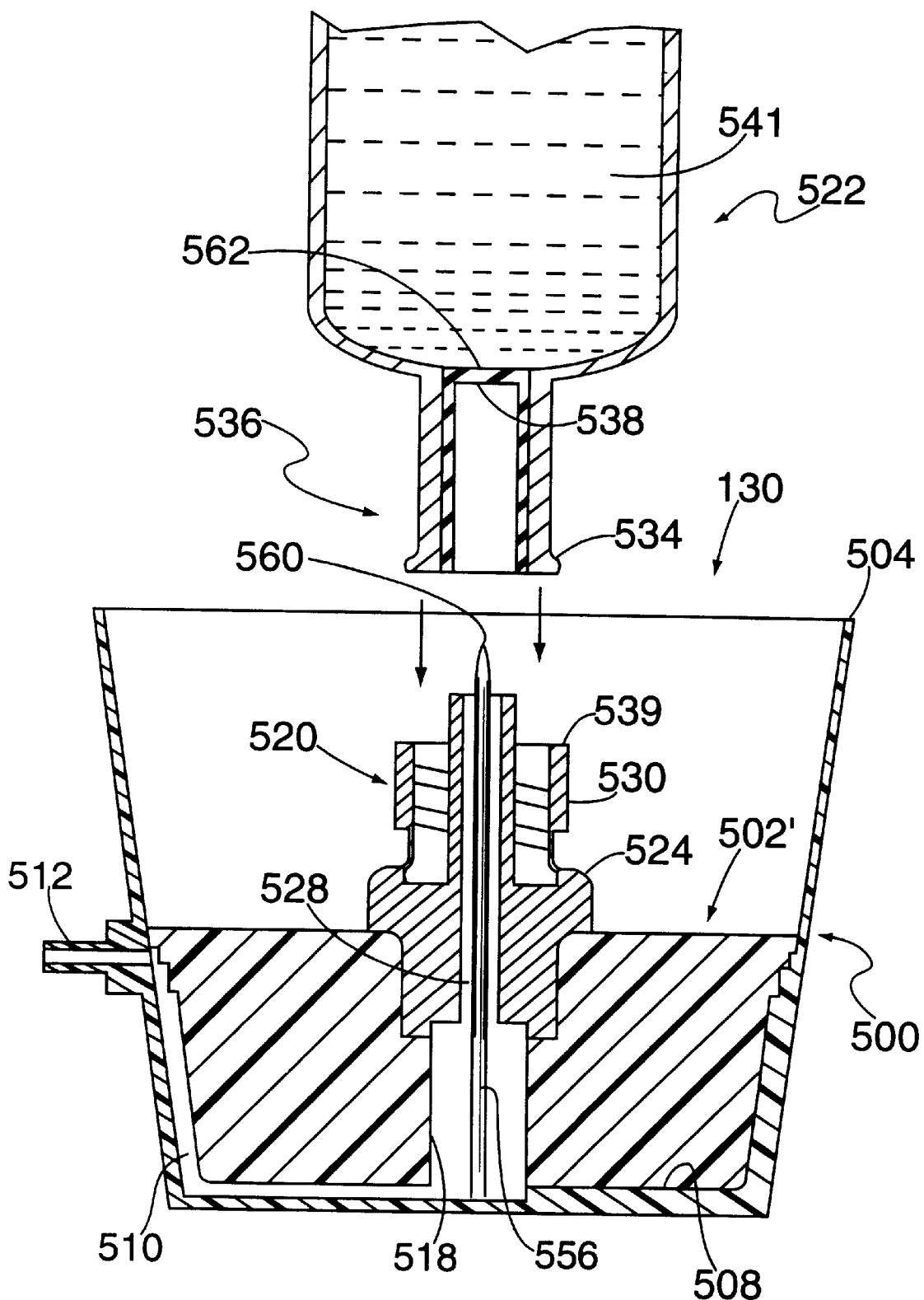
FIG. 12 is an exploded sectional view of another embodiment utilizing a needle for puncturing a sealed luer connector associated with the supply of the first or second component prior to attachment to the reservoir.
Figure 13:
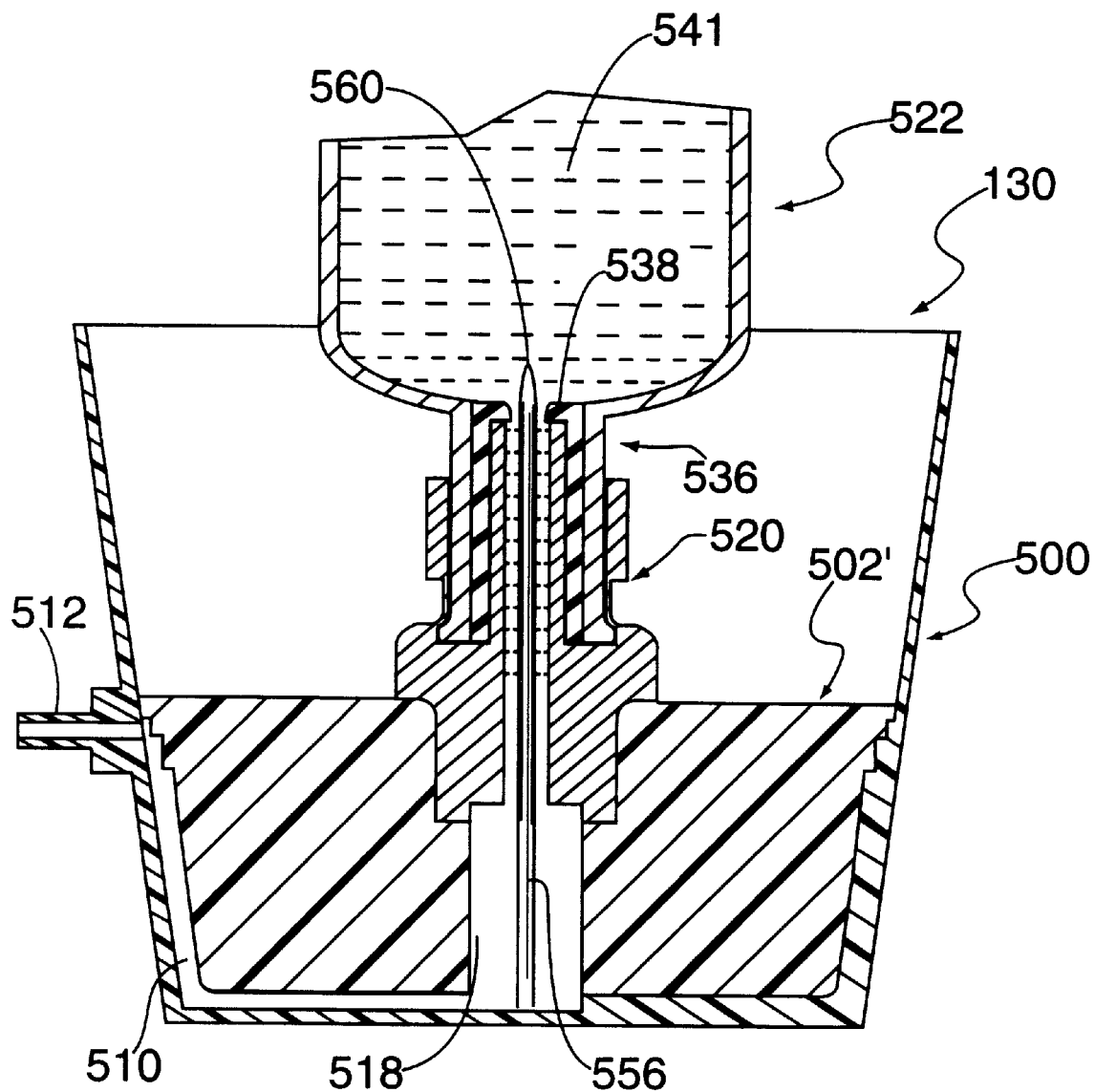
FIG. 13 is a sectional view of the embodiment depicted in FIG. 12, showing the supply of the first or second component attached to the reservoir.

Referring now to another embodiment shown in FIGS. 12 and 13, there is shown an arrangement wherein a needle 556 is provided in the reservoir basin 500 to break a frangible seal 538 disposed in neck portion 536 of the supply 522. This configuration utilizes a smaller insert 502' to minimize the likelihood of inadvertent needle pricks by medical personnel. The needle 556 is attached to the base 508 of the basin 500, and extends coaxially through the hollow bore 518 in the insert 502' and the hollow bore 528 in luer connector 520, such that the tip 560 of the needle 556 is exposed above the rim 539 of the central portion 526 of the luer connector 520, but below the rim 504 of the basin. The frangible seal 538 resides in the neck portion 536 of the supply 522 and covers the opening 562 to retain the first or second component inside the internal chamber 541 of the supply 522. As shown in FIG. 13, the supply 522 is attached to the reservoir 130 by inserting the male connector 534 into the female luer connector 520 until the needle 556 punctures the seal 538.

Figure 14:
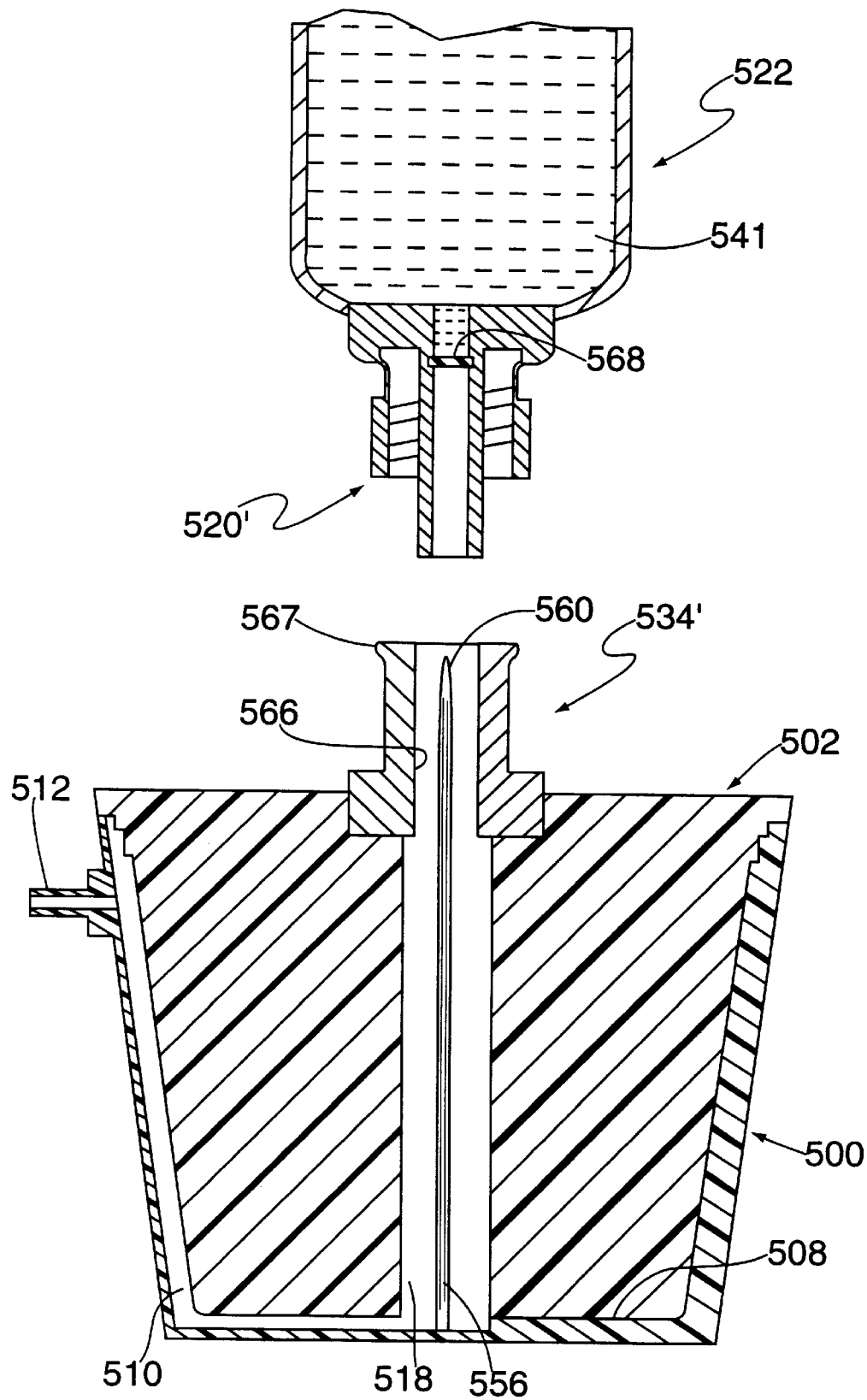
FIG. 14 is an exploded sectional view of a modification of the embodiment shown in FIGS. 12, 13, with the luer connectors reversed.
Figure 15:
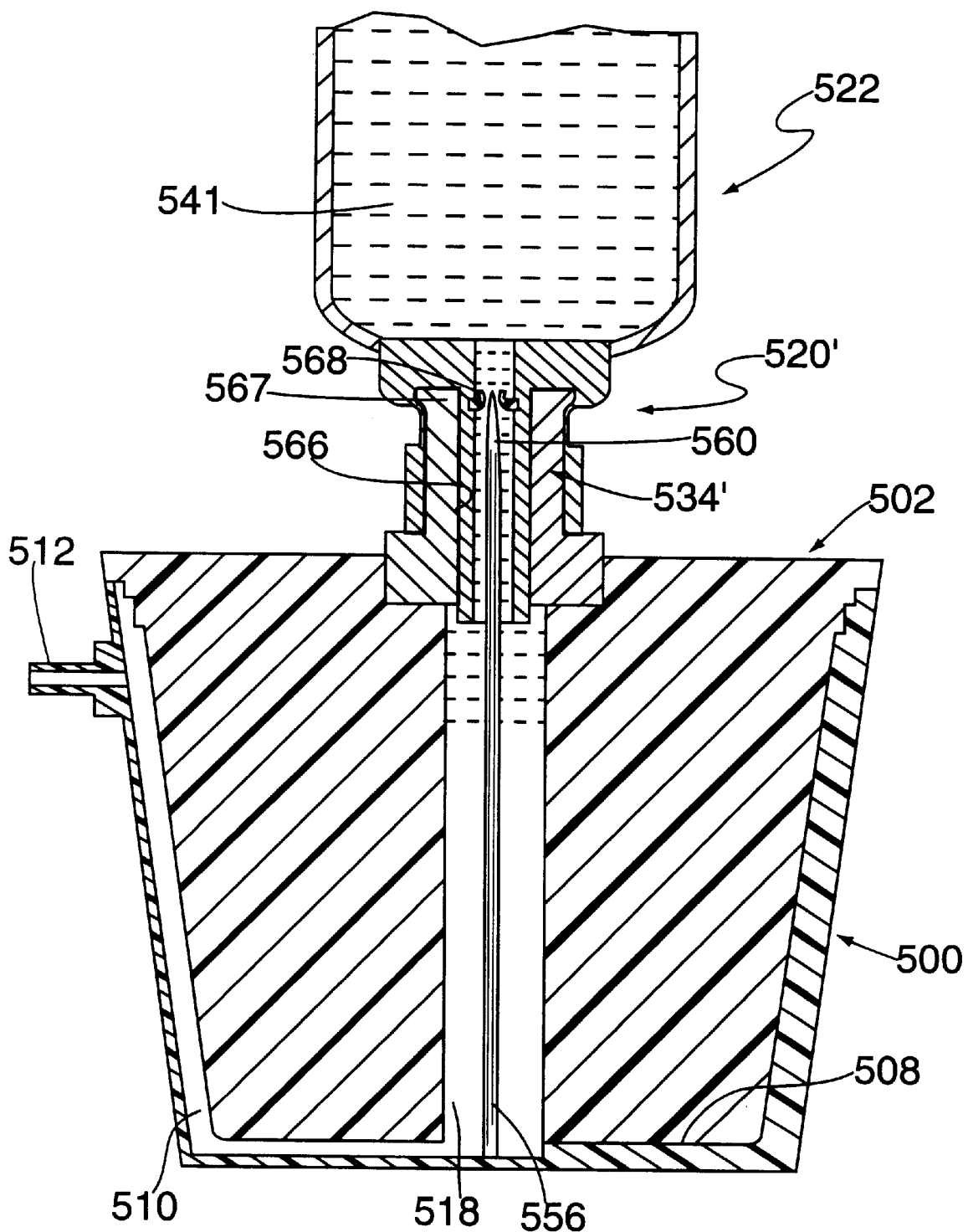
FIG. 15 is a sectional view of the embodiment of FIG. 14, showing the supply of the first or second component attached to the reservoir.

In yet another embodiment depicted in FIGS. 14 and 15, the arrangement of the luer connectors is reversed with respect to the insert 502 and the supply 522. Specifically, a female luer connector 520' is integral with the supply 522, and is adapted to receive a male luer connector 534' integral with the insert 502. In this configuration, a needle 556 attached to the base 508 of the basin 500 is provided as described above. The needle 556 extends coaxially through the hollow bore 518 of the insert 502 and partially through the hollow bore 566 of the male luer connector 534'. The tip 560 of the needle 556 resides below the flared edge 567 of the male luer connector 534' to minimize the likelihood of a pin-prick. A frangible seal 568 is disposed across the hollow bore 528' of the female luer connector 520'. When the supply 522 is connected to the reservoir 130 as described above, the tip 560 of the needle 556 punctures the seal 568, causing the liquid to flow into the reservoir 130 from the storage volume 541 as shown in FIG. 15.

The foregoing reservoir embodiments depict connections to a supply of the first or second component in the form of a container. It is anticipated that the same connector configurations may be made to a remotely disposed supply, wherein the reference numeral 522 represents a fluid contact interface such as an elongated tube or the like.

Figure 16:
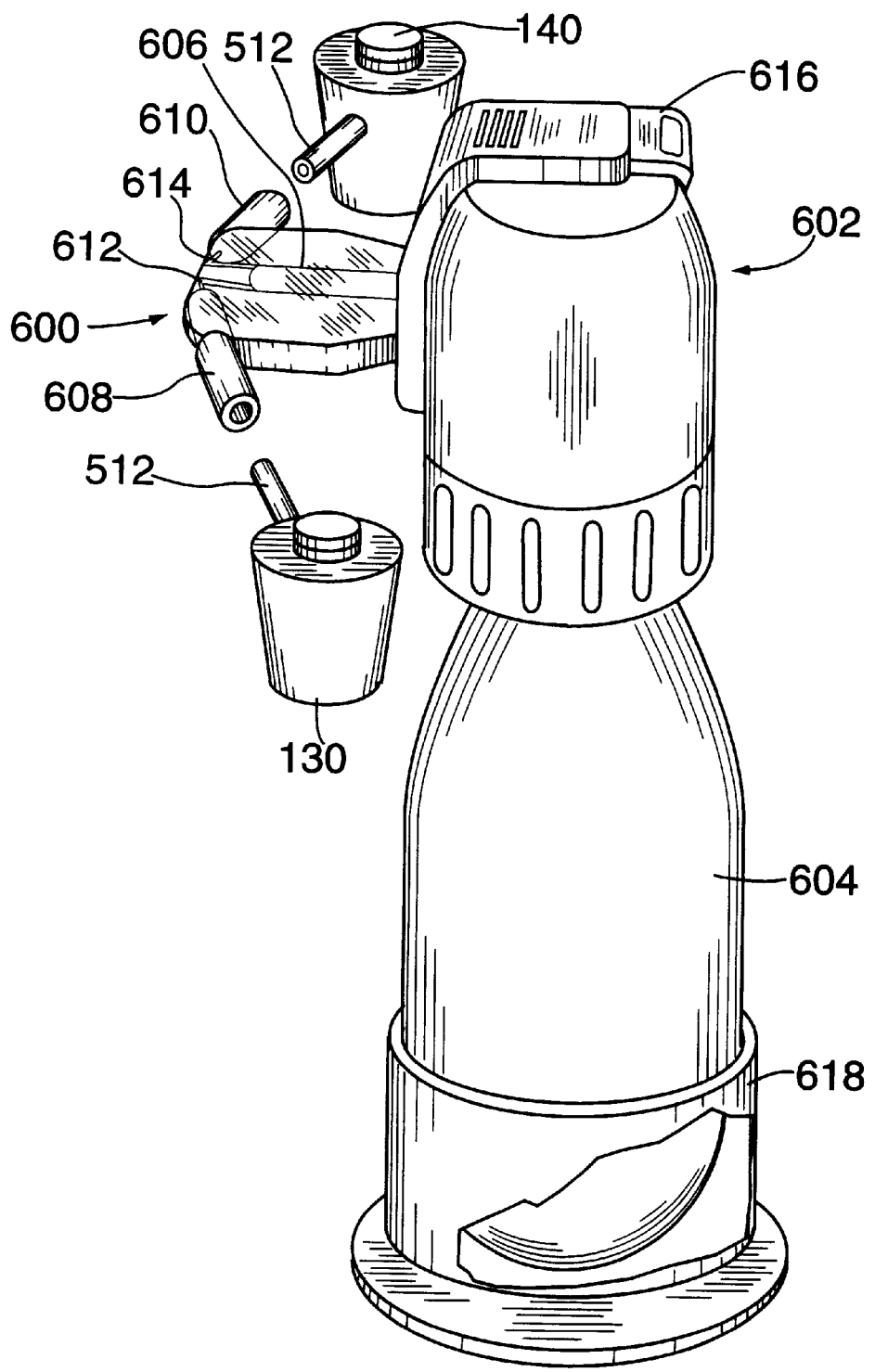
FIG. 16 is another embodiment of an applicator with a spray head having integrally molded passageways.
Figure 17:
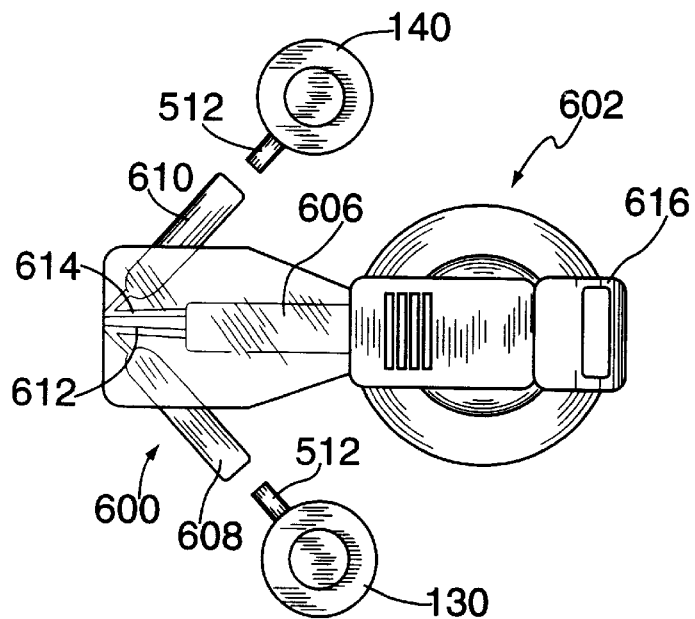
FIG. 17 is a top plan view of the applicator shown in FIG. 16.

Referring now to FIG. 16, there is shown another embodiment of the applicator comprised of a spray head 600, housing 602 and a compressed air cartridge 604. The principle of operation is essentially the same as that described in the foregoing. The spray head 600 includes integrally molded passageways for communicating a supply of pressurized gas to dispense the respective biological fluids 132, 142 from reservoirs 130, 140, respectively. The spray head 600 defines a centrally disposed gas plenum 606 communicating with a first conduit 608 and a second conduit 610, respectively communicating with reservoirs 130, 140. The pressurized gas travels from the gas plenum 606 through first and second nozzle bores 612, 614, respectively, which terminate in nozzle openings in the spray head 600. In this manner, the respective first component and second component are drawn out of the reservoirs 130, 140 and expelled through the nozzle openings. The principle of operation is generally the same as that described above, except that the internal bores of conduits 608, 610 or the nozzle bores 612, 614 may be relatively modified in cross section so as to vary the flow rate between the respective component fluids to adjust the dispensed ratio.

The main body 602 includes a trigger mechanism 616 as described above the with respect to the previous embodiments. A compressed gas cartridge 604 is threadably connected to the housing 602 in a manner similar to that shown in FIG. 2B. A receptacle/holder 618 is adapted for supporting the apparatus around the compressed gas cartridge 604 as shown in FIG. 16.

Figure 18:
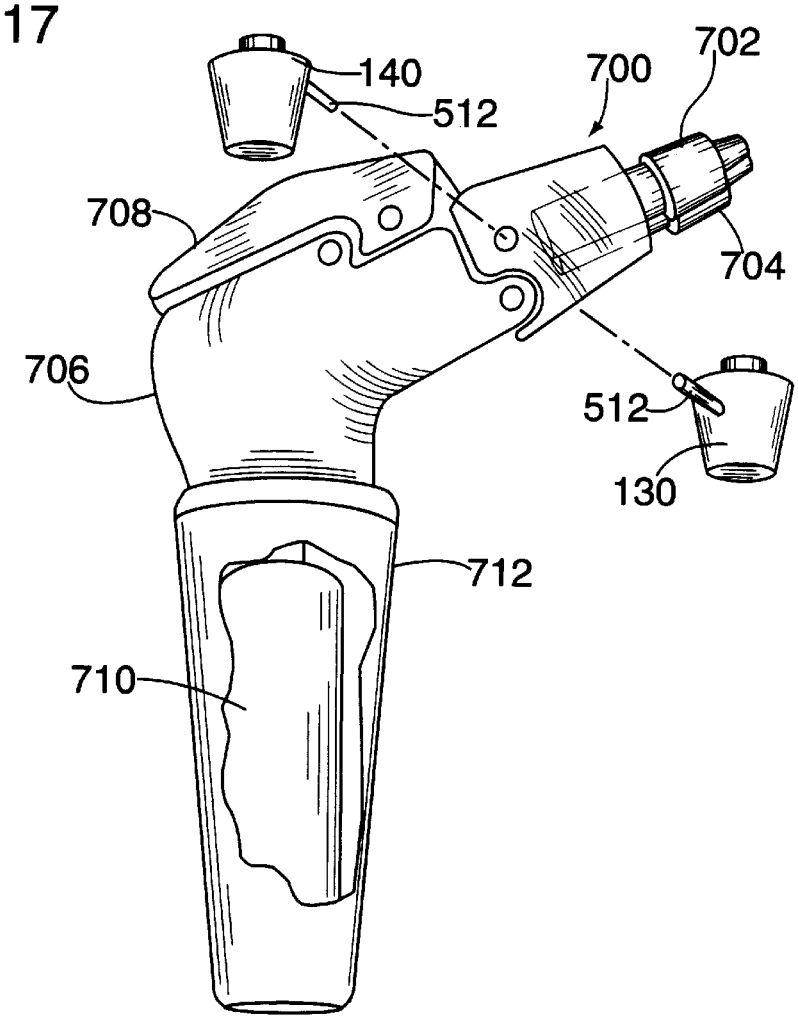
FIG. 18 is a perspective view of another applicator design.

FIG. 18 depicts another embodiment of an applicator having a spray head 700 including independent nozzles 702, 704, and a housing 706 having a trigger 708 which covers the entire top portion of housing 706 to facilitate an enhanced grip during operation. A compressed gas cartridge 710 is located within a removable cover 712 which is attached to the main body 706 as shown.

Figure 19:
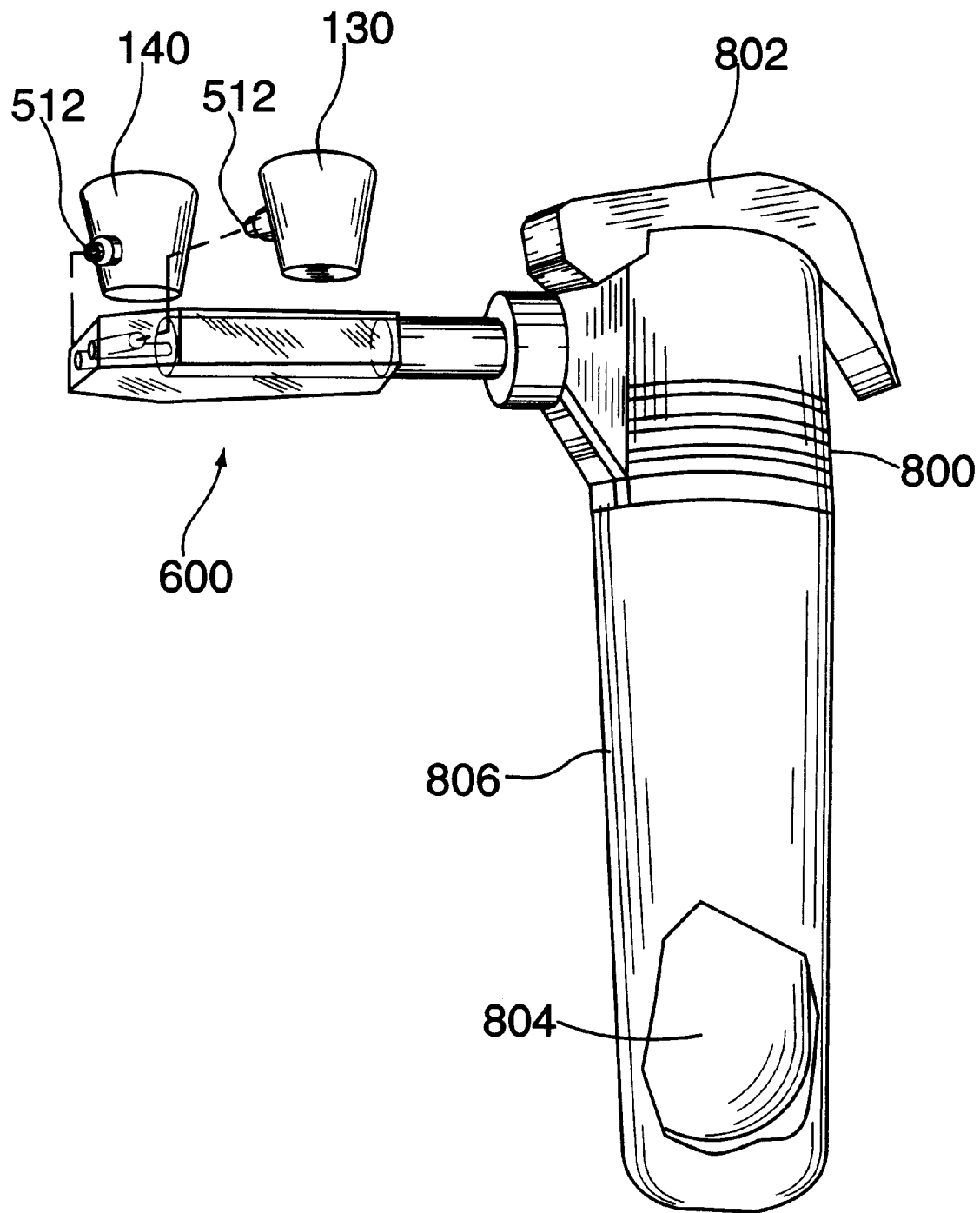
FIG. 19 is a perspective view of yet another applicator design.

In yet another alternative of the embodiment shown in FIG. 19, the spray head 600 of the embodiment shown in FIG. 16 is associated with a housing 800 similar to that shown in FIG. 18, having a similar trigger arrangement 902. The gas cartridge 804 is similarly disposed within a removable cover 806.

The present invention has been shown and described in what are considered to be the most practical and preferred embodiments. It is anticipated, however, that departures may be made therefrom and that obvious modifications will made by those skilled in the art.

I claim:

1. An applicator for creating a homogeneous film coating of a substance comprising a first component and a second component, the applicator comprising:
    a housing having a first dispensing conduit for dispensing said first component and a second dispensing conduit for dispensing said second component;
    a pressure supply conduit in communication with said dispensing conduits;
    a first reservoir containing said first component, said first reservoir being in communication with said first dispensing conduit;
    a second reservoir containing said second component, said second reservoir being in communication with said second dispensing conduit;
    said first reservoir and second reservoir each including a luer connector for attaching a supply of said first component to said first reservoir and a supply of said second component to said second reservoir.

2. The applicator recited in claim 1, further comprising:
    a first pressure regulator in communication with said first reservoir for controlling pressure supplied through said pressure supply conduit to said first reservoir; and
    a second pressure regulator in communication with said second reservoir for controlling pressure supplied through said pressure supply conduit to said second reservoir.

3. The applicator recited in claim 1, wherein said first reservoir and said second reservoir each comprises:
    a reservoir basin having a sidewall and a base, said sidewall including a fluid outlet for communicating said first reservoir with said first dispensing conduit and said second reservoir with said second dispensing conduit; and
    an insert disposed in and integral with said reservoir basin, said insert having said luer connector integral therewith.

4. The applicator recited in claim 3, wherein said first reservoir and said second reservoir each further comprises a channel defined in said base and said sidewall of said reservoir basin, said channel extending to said sidewall from a center portion of said base, and along said sidewall from said base to said fluid outlet.

5. The applicator recited in claim 3, wherein said first reservoir and said second reservoir each further comprises a needle disposed coaxially with said reservoir luer connector for puncturing a frangible seal associated with said supply of said first component when said supply of said first component is connected to said first reservoir and a frangible seal associated with said supply of said second component when said supply of said second component is connected to said second reservoir.

6. The applicator recited in claim 3, wherein said supply of said first component and said supply of said second component includes a frangible seal disposed over an outlet associated with said supply, said frangible seal being positioned so as to be broken by connecting said first reservoir to said supply of said first component and said second reservoir to said supply of said second component.

7. The applicator recited in claim 1 including:
    a spray head having said first dispensing conduit, said second dispensing conduit, and said pressure supply conduit in communication with said dispensing conduits; and
    said housing having a pressure supply conduit in communication with said pressure supply conduit in said spray head.

8. The applicator recited in claim 7, wherein said first dispensing conduit has a diameter different from that of said second dispensing conduit to vary the ratio of said first component to said second component dispensed from said spray head.

9. The applicator recited in claim 7, further comprising a cartridge containing a biologically compatible compressed gas, said cartridge being attachable to said pressure supply conduit in said housing for communicating said pressurized gas from said cartridge to said pressure supply conduit.

10. An applicator for creating a homogeneous film coating of a biological adhesive, the adhesive comprising a first component and a second component, the applicator comprising:
    a housing having a first dispensing conduit for dispensing said first component and a second dispensing conduit for dispensing said second component;
    said housing defining a pressure supply conduit in communication with said dispensing conduits, said pressure supply conduit adapted for communicating with a pressurized gas from a detachable cartridge;
    a first reservoir containing said first component, said first reservoir being in communication with said first dispensing conduit;
    a second reservoir containing said second component, said second reservoir being in communication with said second dispensing conduit;
    a first pressure regulator in communication with said first reservoir for controlling pressure supplied through said pressure supply conduit to said first reservoir; and
    a second pressure regulator in communication with said second reservoir for controlling pressure supplied through said pressure supply conduit to said second reservoir.

11. The applicator recited in claim 10, wherein said housing defines a chamber for receiving said cartridge in fluidic communication with said pressure supply conduit.

12. The applicator recited in claim 10, wherein said cartridge contains pressurized carbon dioxide.

13. An applicator for creating a homogeneous film coating of a substance comprising a first component and a second component, the applicator comprising:
- a housing having a first dispensing conduit for dispensing said first component and a second dispensing conduit for dispensing said second component;
- said housing defining a pressure supply conduit in communication with said dispensing conduits;
- a cartridge containing a biologically compatible compressed gas, said cartridge being attachable to said pressure supply conduit for communicating said pressurized gas from said cartridge to said pressure supply conduit;
- a first reservoir containing said first component, said first reservoir being in communication with said first dispensing conduit;
- a second reservoir containing said second component, said second reservoir being in communication with said second dispensing conduit;
- a first pressure regulator in communication with said first reservoir for controlling pressure supplied through said pressure supply conduit to said first reservoir; and
- a second pressure regulator in communication with said second reservoir for controlling pressure supplied through said pressure supply conduit to said second reservoir.

* * * * *